US007077967B2

(12) United States Patent
Perkins et al.

(10) Patent No.: US 7,077,967 B2
(45) Date of Patent: *Jul. 18, 2006

(54) POULTRY PROCESSING WATER RECOVERY AND RE-USE PROCESS

(75) Inventors: Michael Perkins, Plantation, FL (US); Joe Phillips, Poquoson, VA (US); Dale Gann, Littleton, CO (US); Richard Miller, Mt. Juliet, TN (US); William McGrane, Ormond Beach, FL (US)

(73) Assignee: Zentox Corporation, Wellesley Hills, MA (US)

( * ) Notice: Subject to any disclaimer, the term of this patent is extended or adjusted under 35 U.S.C. 154(b) by 535 days.

This patent is subject to a terminal disclaimer.

(21) Appl. No.: 10/045,778

(22) Filed: Jan. 11, 2002

(65) Prior Publication Data

US 2003/0094422 A1    May 22, 2003

Related U.S. Application Data

(63) Continuation-in-part of application No. 09/507,163, filed on Feb. 18, 2000, and a continuation-in-part of application No. 09/591,513, filed on Jun. 9, 2000, now Pat. No. 6,605,253.

(60) Provisional application No. 60/261,012, filed on Jan. 11, 2001.

(51) Int. Cl.
   *C02F 1/78* (2006.01)
(52) U.S. Cl. ............... 210/760; 210/708; 210/764; 210/776; 210/800; 210/805
(58) Field of Classification Search ............ 210/754, 210/760, 764, 776, 800, 805, 708
   See application file for complete search history.

(56) References Cited

U.S. PATENT DOCUMENTS 3,314,880 A    4/1967    Rubin .................. 210/44

(Continued)

FOREIGN PATENT DOCUMENTS

EP    0 353 314 A1    8/1988

(Continued)

OTHER PUBLICATIONS

"Preozonation as a Coagulant Aid in Drinking Water Treatment", B.M. Saunier et al. *Research & Technology Journal AWWA*, May 1983, 99 239-246.

(Continued)

*Primary Examiner*—Betsey Morrison Hoey
(74) *Attorney, Agent, or Firm*—Brown Rudnick Berlack Israels LLP; John C. Serio

(57) ABSTRACT

The inventions of the present disclosure are directed to processes designed to recover water used in certain aspects of the processing of poultry, treat the recovered water to remove solids, fats, oils and greases, animal proteins and pathogenic organisms and to reuse the treated water for poultry processing operations. The processes described herein reduce bacteria and microorganisms associated with the poultry and reuse water. The present disclosure can be employed with an approach that includes unexpected positive results of reacting ozone and chlorine with water being treated for reuse to generate hypochlorous acid and/or other effective biocides. Ozone reacts with fats, oils, and greases, dissolved in the reuse water, to produce specific surface-active agents and surfactants which reduce the surface tension of the water which it is dissolved. The combination of these surface-active agents and surfactants and the biocides cause an extraordinary release and destruction of bacteria from the poultry carcass as well as the reuse water.

20 Claims, 10 Drawing Sheets

U.S. PATENT DOCUMENTS

| | | | | |
|---|---|---|---|---|
| 3,350,301 A | 10/1967 | Hoffman | | 210/44 |
| 3,732,163 A | 5/1973 | Lapidot | | 210/47 |
| 3,912,533 A | 10/1975 | Heyer | | 127/13 |
| 3,945,918 A | 3/1976 | Kirk | | 210/44 |
| 3,951,795 A | 4/1976 | Doncer et al. | | 210/61 |
| 4,021,585 A | 5/1977 | Svoboda et al. | | 426/332 |
| 4,277,334 A | 7/1981 | Ruidisch et al. | | 210/154 |
| 4,309,388 A | 1/1982 | Tenney et al. | | 422/304 |
| 4,481,080 A | 11/1984 | Mallon | | 201/31 |
| 4,517,159 A | 5/1985 | Karlson | | 422/20 |
| 4,608,165 A | 8/1986 | Galper | | 210/232 |
| 4,744,903 A | 5/1988 | McAninch et al. | | 210/632 |
| 4,744,904 A | 5/1988 | McAninch et al. | | 210/632 |
| 4,790,943 A | 12/1988 | Dunn et al. | | |
| 4,827,727 A | 5/1989 | Caracciolo | | 62/63 |
| 4,844,189 A | 7/1989 | Shisgal et al. | | 177/211 |
| 4,849,237 A | 7/1989 | Hurst | | 426/332 |
| 4,868,950 A | 9/1989 | Harben, Jr., deceased | | 17/11.2 |
| 4,876,004 A | 10/1989 | Verhoeff | | 210/170 |
| 4,947,518 A | 8/1990 | Covell, III | | 17/11.2 |
| 4,966,713 A | 10/1990 | Keys et al. | | 210/705 |
| 5,053,140 A | 10/1991 | Hurst | | 210/704 |
| 5,132,010 A | 7/1992 | Ossenkop | | 210/121 |
| 5,173,190 A | 12/1992 | Picek | | 210/651 |
| 5,178,755 A | 1/1993 | LaCrosse | | 210/195.1 |
| 5,227,184 A | 7/1993 | Hurst | | 426/312 |
| 5,248,439 A | 9/1993 | Derrell | | 210/708 |
| 5,264,229 A * | 11/1993 | Mannig et al. | | 426/335 |
| 5,514,282 A | 5/1996 | Hibbard et al. | | 210/652 |
| 5,593,598 A | 1/1997 | McGinness et al. | | 210/748 |
| 5,728,305 A | 3/1998 | Hawkinson | | 210/760 |
| 5,759,415 A | 6/1998 | Adams | | 210/776 |
| 5,882,253 A | 3/1999 | Mostoller | | 452/173 |

FOREIGN PATENT DOCUMENTS

| | | |
|---|---|---|
| EP | 0 331 296 A1 | 2/1989 |
| EP | 0 468 461 A1 | 7/1991 |

OTHER PUBLICATIONS

"Ozone as a Coagulant Aid", D. Reckhow et al., *AWWA Seminar Proceedings No. 20005*, 1986, pp. 17-46.

* cited by examiner

POULTRY PROCESSING WATER RECOVERY AND RE-USE PROCESS

CROSS-REFERENCE TO RELATED APPLICATIONS

This patent application is a continuation-in-part of U.S. Utility patent application Ser. No. 09/507,163, filed in the U.S. Patent and Trademark Office (USPTO) on Feb. 18, 2000 by Perkins et al. and a continuation-in-part of U.S. Utility patent application Ser. No. 09/591,513, filed in the U.S. Patent and Trademark Office (USPTO) on Jun. 9, 2000 now U.S. Pat. No. 6,605,253 by Perkins et al., and claims priority to U.S. Provisional Application Ser. No. 60/261,012 filed in the USPTO on Jan. 11, 2001 by Perkins et al., the entire contents of each of these applications being hereby incorporated by reference herein.

BACKGROUND

1. Technical Field

The present disclosure relates generally to the field of carcass processing, and more particularly, to a water disinfection, recovery and re-use process used in the processing of poultry.

2. Background of the Related Art

A typical poultry processing plant receives live animals from the grow-out farms, slaughters the animals, drains the blood and then removes the feathers, "paws," heads and detritus in the initial stages of processing. The carcasses are then sent to mechanized evisceration where the internal organs, digestive tract and other edible and inedible parts are removed. In typical operations, some of the internal organs (i.e., heart, liver and gizzards) are harvested for food products. The carcasses are thereafter sent by way of mechanized line operations through a series of washing and sanitizing steps before the product is shipped as "fresh" product or packaged for freezing. These line operations typically consume large quantities of water.

Accordingly, the poultry processing industry has generally been characterized as a large volume consumer of water in conducting the slaughter, processing and packing of animals for both human consumption and other uses. Recent initiatives by the United States Department of Agriculture (USDA), under the jurisdiction of the Food Safety Inspection Service (FSIS), have resulted in a further increase in the volume of water used to wash poultry carcasses to meet the more stringent requirements of "0 pathogen tolerance".

In addition, poultry industry interests have been actively seeking methods of reducing the consumption of water due to economic reasons and, additionally in some cases, because of limited availability of sufficient volumes of water to meet the processing requirements. Still other considerations involving limited water treatment resources have raised the need to reduce water consumption. It is therefore an object of the present invention to provide new solutions to reducing the volume of water required for processing poultry or other foodstuffs.

Prior processes have not focused on the need to conserve water from an economic perspective and accordingly, while they may generally involve water reuse applications, their approaches have failed to address critical economic restrictions inherent in poultry and other food processing operations. It is yet another object of the present invention to provide water reuse processes which are economically feasible and which provide improved savings to the food-preparing manufacturer.

Typical of prior approaches have been efforts directed to the recovery, treatment and recycle of poultry chiller bath water in a closed loop and "semi-closed loop" type of process where water from the chiller baths is treated to remove solids, fats, oil, grease, organic compounds and microorganisms before reintroducing the treated water to the chiller baths.

These efforts may be characterized as primarily aimed at reducing the electrical power considerations in chilling the water used in these systems of processing operations. These goals are generally met by reusing the already cooled chiller water and trying to reintroduce the already chilled water back into the chiller makeup feed water, thereby reducing the temperature of incoming fresh water. However, the recovery of used chiller bath process water brings with it a very high contamination burden requiring extensive treatment. Representative examples of such approaches have been described in U.S. Pat. Nos. 5,728,305; 5,173,190; 5,178,755; 5,053,140; 4,790,943; and 5,593,598. While such approaches have had some limited success in addressing the treatment challenges, they have to date proven to be of questionable economic value to the industry. It is still another object of the present invention to address such deficiencies with new approaches and devices, which are economically sensitive.

Prior efforts have also generated a substantial number of devices designed to provide some filtering efforts. U.S. Pat. Nos. 5,759,415; 5,248,439; 5,132,010; 4,876,004; 4,844,189; 4,481,080 and 3,912,533 provide representative examples of such devices. As will be readily noted, some are structurally complex requiring substantial capital expenses and others, while simpler in structure, are aimed at solving different needs. For example, U.S. Pat. No. 4,481,080 shows a series of printouts separated by baffles for equalizing the residence times of large and small particles. It has been discovered that such solutions are either unnecessarily complex or are unnecessary altogether. It is another aspect of the present invention to provide devices useful in water recovery and treatment methods, which avoid such deficiencies and solve the needs of removing gross levels of contaminants quickly, effectively and economically.

In several of the inventions referenced the inventors have directed their efforts at chilled water reuse claiming significant savings in Btu requirements. The devices employed have focused upon the recovery, treatment and reuse of the USDA required 0.5 gallon per bird overflow. While the technical approaches may differ from invention to invention, they share the disadvantages that the source of their water (i.e., bird chiller water) contains a significant and high quantity of organic contaminants as compared to the sources that are identified by the inventors herein, and the volumes available for recovery are limited strictly to the USDA mandated 0.5 gallon per bird limitation. It is yet another object of the present invention to avoid the disadvantages associated with such prior art approaches.

SUMMARY

The various objects and aspects of the present invention are met using an approach which focuses on the source of the process water to be recovered and reused. This is in contrast to prior approaches which have focused upon the recovery and reuse of the "communal bath" chiller water. These conventional approaches commonly suffer from difficult treatment challenges and typically require fairly sophisticated treatment equipment components. As a result, these approaches have been accompanied by disadvantageously high capital and operating costs.

In one particular embodiment in accordance with the principles of the present disclosure, the inventive approach of the present invention includes processes which allow for the safe and economic recovery, treatment and reuse of certain poultry processing water, specifically including the "carcass final rinse," "inside/outside carcass rinse," "water rails" or, water sprays used in the inspection process for the inspectors to wash their hands and instruments, flume transport of various animal parts and other smaller streams with respect to poultry processing operations while avoiding exclusive use of communal chiller bath water.

The present disclosure contemplates implementing a water reuse program that returns reuse water that has been disinfected with ozone and then chlorinated at an advantageous dosage before being reintroduced to the production process at an upstream point, such as in the scalder or similar heating portion of the processing steps. The reintroduction of the chlorinated reuse water into the scalder or similar heating processing step causes a dramatic reduction in the levels of microorganisms associated with the carcasses that have not been found in the prior art. Also, the present disclosure further contemplates introducing chlorinated and/or ozonated water, for example, along the foodstuffs processing steps, such as along the points where the use of heated water is applicable, such as in the scalder or similar processing steps which subject the carcasses to heated water. In such heated processing steps, the pores and tissue membranes of the carcasses are open and are more readily receiving of the surrounding water, i.e., the chlorinated and/or ozonated water, thereby having greater efficacy to the removal of microorganisms associated with such foodstuff processing.

It is envisioned that in certain circumstances chiller bath overflow water may be used as one of the water sources if such chiller water can be sufficiently diluted with water from other sources. The intended points of re-use for this recovered and treated water have been identified as chiller bath water, evisceration wash water, defeathering water and other "non-product contact" processes. Additionally, in those plants where transport of process water is complicated due to plant layout and physical design an improved device is provided for effecting an economic and efficient recovery system comprising a recovery sump with a continuing overflow to permit removal of soiled water, grease and oils.

In an alternate embodiment, the present disclosure employs an approach which focuses on appropriately regulating and controlling the pH of process water to be disinfected through addition, regulation and control of a disinfecting agent. The control of pH and level of disinfecting agent is implemented throughout multiple steps in the production process including any process water to be recovered and reused. This is in contrast to prior approaches which have failed to appreciate the benefits associated with pH control, multiple point controlled treatment, or even the unexpected advantages to be gained by reducing the organic loads within such process water.

In yet another alternate embodiment, the present disclosure can be employed with an approach that includes the unexpected positive results of reacting ozone and chlorine with water being treated for reuse to generate hypochlorous acid and/or other effective biocides. Ozone reacts with animal fats, generally known as fats, oils, greases, and/or lipids, etc., dissolved or contained in the reuse water, to produce specific surface-active agents and surfactants which reduce the surface tension of the water which it is dissolved.

The combination of these surface-active agents and surfactants and the biocides cause an extraordinary release and destruction of bacteria from the poultry carcass as well as the reuse water.

Advantages of the present invention include processes which allow for the automated regulation of the pH of poultry processing water, preferably at certain stages of the process, so as to dramatically improve the efficiency and effectiveness of antimicrobial or other disinfection agents added. The poultry process treatment water which can especially benefit includes the water used in poultry scalding, picking, post-pick washing, evisceration, carcass washing and other stages of poultry processing designed to physically remove any fecal matter, ingesta and other digestive tract remnants from the slaughter and evisceration processes. Additionally, an improved device and method are provided for effecting economic and efficient regulation of disinfection agent and control of the disinfection chemistry throughout the multiple steps of the production process.

Physical removal of visible fecal material and other contaminants from poultry carcasses will be carried out by serial carcass washing steps (e.g., scalder, picker, post pick spray wash, inside/outside carcass washing cabinets and outside carcass washing cabinets) where medium pressure, high volume water spraying is employed. The introduction of USDA approved antimicrobial agents (e.g., calcium hypochlorite or others), applied at optimum pH control level for chlorine disinfection at multiple treatment stages (e.g., scalder, picker, post pick spray wash, inside/outside carcass wash and outside carcass wash) and using the best practical control methods is designed to significantly reduce microbial levels on all carcasses prior to and after their entry into the submersion chiller system. Aspects of the present invention described herein are designed to employ the advantages of controlled chlorination (e.g., calcium hypochlorite and/or other USDA approved food grade biocides) at optimum pH levels, together with the effectiveness of increased contact time (CT) through the implementation of multiple stage treatment of the carcass during slaughter, evisceration, washing and chilling.

Additionally, the present disclosure provides for effecting economic and efficient regulation of disinfection agent effectiveness comprising a system and method for removing a major portion of filterable materials including fats, oils and greases (FOG), total suspended solids (TSS), proteins, blood products, lipids and other materials represented as total chemical oxidation demand (COD) from the chiller tank water.

Aspects of the presently disclosed disinfection process for use in the processing of foodstuffs are designed as an intervention step in poultry processing to allow for continuous on-line processing of poultry carcasses that may have accidentally become contaminated during the evisceration process. Such on-line processing is designed to replace the need for off-line manual washing and cleaning of the contaminated carcasses. By eliminating such off-line manual washing, food safety will be enhanced due to the elimination of the physical handling of carcasses and the cross-contamination that may result from such physical handling. An additional benefit is that it will be possible to run the production process with a reduced number of interruptions, which will result in a more efficient production process.

The disinfection process according to the present invention can include: the removal, using the processing plant's existing washing, spraying and mechanical scrubbing devices (modified if required), of visible fecal material or other contaminants from the carcasses resulting from the mechanical evisceration process; the introduction of an enhanced antimicrobial treatment agent at multiple stages to improve food safety by reduction of total microbial levels; the improvement of disinfection in the facility's overall production process including the carcass chiller system through the use of pH controlled chlorination to further reduce microbial counts, and the reduction of the amount of physical handling of carcasses and therefore, reduction of the potential for cross-contamination.

Further, the present invention is specifically designed to be easily incorporated into the processor's existing production equipment and plant layout. This ease of implementation is accomplished by using, to the greatest extent possible, the processor's existing carcass wash stations, scalders, pickers and other designated treatment points as the point of treatment by using the existing water piping and delivery systems as the means of delivery of the invention's chemical and disinfection enhancements.

The invention described herein is designed to meet the current USDA regulations for removal of visible fecal material using the plant's existing washing, spraying and mechanical scrubbing devices, and to reduce microorganism counts and improve food safety, all in a more cost effective and environmentally friendly manner than other approaches.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

DETAILED DESCRIPTION OF PREFERRED EMBODIMENTS

Figure 1:
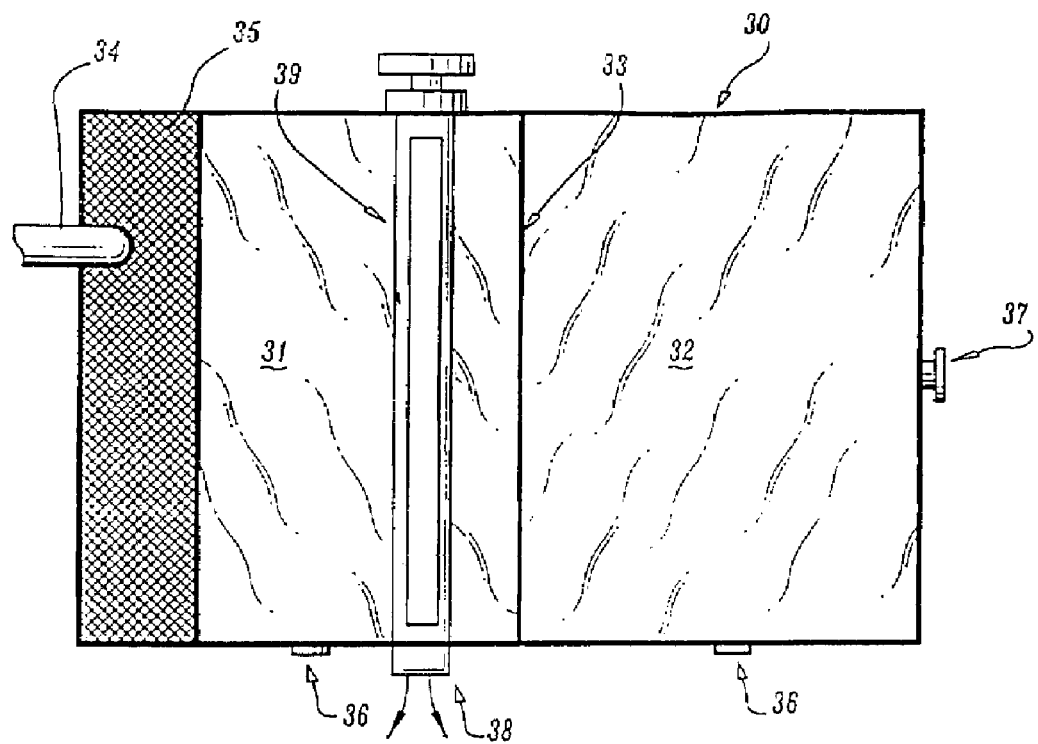
FIG. 1 is a top plan view illustrating one particular embodiment of a recovery sump device, in accordance with the present disclosure.

The preferred embodiments of the apparatus and methods disclosed herein are discussed in terms of poultry processing water disinfection processes. It is envisioned, however, that the disclosure is applicable to a wide variety of processes including, but not limited to general carcass processing, etc. The following discussion includes an explanation of relevant terminology, a description of instrumentation employed for poultry processing and water disinfection, in accordance with the present disclosure, followed by a description of the preferred processes associated therewith.

A poultry processing line includes multiple processing steps. One step involves a poultry carcass being immersed in a chiller tank and is referred to as the "chilling step." During the chilling step, temperature of the poultry carcass is cooled as a result of immersion in a cold water bath. The "chilling step" is significantly different from other processing steps such as scalding, picking, evisceration, and various washing steps. These steps are referred to as "non-chilling processing steps."

Water in the chiller tank is significantly different from water in the various non-chilling steps in terms of organic loading and temperature. The poultry carcass is placed in the chiller tank to cool the carcass to a temperature which inhibits the growth of pathogens. Carcasses entering the chiller tank may be as warm as 100° F. Carcasses exiting a chiller can be cooled to approximately 34–38° F.

The chiller tank is a communal tank that can hold hundreds of poultry carcasses for 1–3 hours, or longer. New carcasses are added to the chiller tank while others exit. Fresh makeup water is added to the chiller tank at a regulated flow rate resulting in a constant rate of overflow from the chiller tank. The water in the chiller tank has an extremely high organic load of both suspended and dissolved organic materials from the poultry carcasses. The organic material is removed to prescribed levels according to regulations, discussed below, for water reuse.

In comparison, the non-chilling processing steps perform quick sprays or dunks of carcasses in water having a temperature of approximately 60–80° F. It is contemplated that wash cabinets spray carcasses for 15 seconds or less, up to an exposure time of approximately 2–3 minutes. The water from non-chilling processing steps has significantly less organic load and is less costly to treat to meet appropriate regulations for reuse.

Further, the non-chilling processing steps are not designed to cool the carcass. It is contemplated that in a typical large-scale processing plant, the total time from killing of a chicken to entering the chiller tank is approximately 5 minutes which includes all non-chilling processing steps.

The present invention will benefit from the application of one or more devices which focus on the source(s) of the process water to be recovered and reused. There are several preferred methods employed in this invention to recover the desired source streams. Plant logistical layout and trench drain system locations as well as elevations determine the appropriate devices used for the capture and recovery of the source streams. In those plants where adequate trench drains at the appropriate elevations are not available the present invention will benefit from the use of a new recovery sump system.

The recovery system contributes to the process' efficiency and economics and it takes advantage of the physical characteristics of the waste stream to be recovered. Specifically, where possible, the recovery sump is designed to allow for a continuous overflow with a screening apparatus to remove, at the source, the greatest mass of floatable solid matter, fats, oils and greases. By implementing this recovery technique, downstream mass removal is advantageously mitigated and the organic loads presented to the floatation, filtration and disinfection/oxidation stages are reduced. This allows for efficient oxidizer usage and the demands of liquid/solid separation are lessened. In cases where the plant layout allows, the capture and recovery method is accomplished by custom designed collection devices located in close proximity to the source and connected by means of piping to a common collection header installed in the plant's existing trench drain system. Further details of the process water recovery sump and collection devices are provided below.

Mechanical Separation/Screening Device and Common Sump

The water collected from the desired source points flows and/or is pumped to the invention's second stage solids separation or screening device. The device consists of a rotary drum, self-cleaning type screening device where solids are captured on wedge wire or other suitable media and the water is allowed to pass through the screen's pours into a sump. The wedge wire mesh size may be varied to best suit the source stream. Additionally, the screening device may be configured in a double or triple drum configuration to allow for different sizes of mesh to sequentially remove solids. The screening device is also fitted with a high pressure, water spraying mechanism to allow for intermittent or, continuous washing of the screen mesh to prevent fouling due to buildup of solids and fats. In a preferred embodiment the screening device is configured as an internal loading screen where water is passed into the center of the drum and passes through a relatively larger mesh size followed by a smaller mesh size on the outer screen. This allows for different size solids to be removed in stages to prevent the fouling of the smaller mesh.

The screening device is driven by an electrical motor and may be fitted with variable speed drive to allow the operator to adjust the drum rotation speed for optimum performance. Varying the speed provides significant operating and performance enhancements by allowing the device to operate at the most efficient speed for washing off the solids. Further, the efficiency of the device can be improved by employment of a traveling spray nozzle. The traveling spray nozzle is installed on a bar fitted with limit switches to define and control the distance of travel of the spray nozzle. The spray nozzle can be driven back and forth across the travel bar by way of electric motor connected to a worm type gear or, by means of water pressure. The screening device is mounted on a sump for collection of the screened water. The sump is fitted with level sensors to control the rate of flow, retention time and any further designed overflow. The sump is also fitted with a dedicated pump to transport the screened water to the treatment system's downstream unit operations for further treatment.

Process Water Surge and Floatation Device

Following passage through the screening device and recovery sump(s), the recovered process water is then advantageously pumped to a device designed to remove remaining floatable solids. The configuration and specific mechanism of the floatation device may employ conventional "dissolved air floatation," "induced air floatation" or, a combination of these techniques for the gas assisted floatation of organic materials such as fat, oil, proteins, lipids, carbohydrates and small solid particles. The floatation vessel also serves to act as a volume-balancing device for hydraulic flows through the system's unit operations. The floatation device serves two distinct functions: 1) it allows for continuous operation of the overall process by containing sufficient volume of water for treatment and, 2) it acts as a floatation and removal basin for the floatable solids, fats, oils and greases. The floatation device is advantageously sized to act as a volume buffer and control to accommodate the variability in source water flows and to assist the entire invention to achieve its desired treatment process rate. This sizing is to allow for the interruption of influent water into the treatment system during any processing downtimes such as breaks for the workers and maintenance shutdowns of the lines. The floatation device is ideally fitted with an air injection system that utilizes compressed air and small bubble diffusion to provide for positive lift for the colloidal oils, grease, fats, undissolved animal matter and proteins present in the stream. The floatation device may also be enhanced by injection of gaseous ozone to promote flocculation of solids as is well known in the art. This flocculation induced by the reaction of ozone is well documented in the literature. The floatation device may also be fed with coagulants, polymers, metal salts or other chemical agents for the purpose of assisting or enhancing solids removal. In a preferred embodiment, the floated matter is removed from the tank by an overflow and skimming device. From there, the process water advantageously passes to the filtration modules which are selected on the basis of need.

Pre-filtration Module:

In this invention, depending on treatment needs, the effluent water from the floatation device will be further treated to remove the smaller solid materials remaining after screening and floatation by means of filtration, electrocoagulation, membrane separation or comparable technology. This module is ideally designed to achieve removal of fats, oils and greases, suspended solids and any inorganic debris. The design of the invention allows for single or multiple filter vessels or electrocoagulation reactors to be advantageously employed at this stage. Additionally, either vacuum type diatomaceous filtration vessels or, pressure type diatomaceous filtration vessels may be used. The present invention also allows for maximum flexibility in the selection of specific grades of the filtration aid, such as diatomaceous earth where diatomaceous earth filtration is employed. In the case of membrane separation, the specific membranes may be sequentially configured to allow for a multiple pass type of separation. Or, in the case of electrocoagulation, reactor size and power input may be varied to provide the maximum efficiency for particle destabilization and separation.

Fine Filtration Module:

Fine filtration of recovered process water is accomplished using diatomaceous earth which is precoated onto a matrix or septum. This fine filtration allows for removal of particulate matter, some adsorption of the fats, oils and greases and suspended solids. Thereafter, the recovered process water is passed to the disinfection and oxidation module and then final polishing. The present invention flexibly allows for the use of single filtration or multiple vessels configured to operate in parallel. Fine filtration may also be configured to allow the use of membrane separation to achieve the desired final filtered water quality. Ideally, the effluent from the fine filtration vessel(s) is continuously monitored by on-line turbidimeters to assure that the target final quality is achieved. In a preferred embodiment, the turbidimeter(s) are interfaced with the main system control panel so that in the event the final water quality from the fine filtration vessel(s) does not meet the designed standard, the entire system can be shutdown by way of a signal feedback loop.

Disinfection and Oxidation Module

The disinfection and oxidation module comprises ozone generation equipment, gas/liquid transfer and mixing devices and the ozone reactor assembly. The ozonation process serves as the primary disinfection and color removal mechanism. The disinfection standard achieved in this module is continuously monitored by an Oxidation Reduction Potential (ORP) probe and conventional electronic voltage measuring devices. The disinfection standard may be pre-determined by input of a specific setpoint (i.e., 750 millivolts—the International Bottled Water Association standard). Any deviation from the desired level of disinfection can be used to alarm, interlock or, alarm and interlock the entire treatment system. Injection of the gaseous ozone is designed to utilize the injection pump's pressure, combined with proper hydraulic pipe sizing to achieve sufficient pressure and flow to promote the maximum mass transfer of the ozone gas into aqueous solution. Either pipe reactor or, high efficiency, centrifugal gas/liquid mixing techniques may be employed. The ozonated water is then pumped to an ozone contact vessel to allow the ozone sufficient time to react with microorganisms to achieve the maximum disinfection standard. Excess ozone gas and unreacted ozone gas is removed by way of off-gas venting in the injection/contact loop. Any ozone off-gas may be reused in the system's floatation device.

Final Polish

The treated water may be advantageously polished after ozonation by means of a settling tank and/or passage through fine media or bag filter(s) or, activated carbon reactor. The need for final polishing will generally be dictated by the specific requirements imposed by the regulatory authorities.

Control and Automation

The process and equipment has the potential to self-regulate and self-monitor with little operator intervention. The use of a programmable logic controller provides the analog and digital input/output capability to continuously monitor and control the system, and to notify the operators of any system upsets and/or maintenance requirements. The process is ideally controlled via a control panel with illuminated displays showing all components operating conditions. The design of the main system control advantageously provides flexibility in choice of options to allow for varying degrees of automation and control sophistication.

Rechlorination:

The treated recovered process water may be chlorinated prior to its introduction into the chiller bath or other designated reuse point. The chlorination of the treated water may be varied in specific dosage to allow for advantageous process application within the processing plant's operations. Again, the required levels of chlorination will generally be dictated by regulatory guidelines or the processors desired chlorine level for specific reuse point applications.

On-line Safety Assurance:

The system is preferably fitted with a turbidimeter which permits instantaneous shut down of the process in the event of a rise in turbidity of the treated water beyond predetermined levels. This would permit the operator to take appropriate remedial action, analyze the water for the presence of pathogens or contaminants and assure that the quality of water introduced into the chiller bath, or other designated reuse points, meets appropriate "safe for the intended use" criteria.

On-Line Backup:

The process is advantageously fitted into the manufacturer's plant's operation with suitable float switches and valves allowing for the introduction of city water in the event that there are any process system malfunctions, upsets or power interruptions. This would then ensure that processing of the food product would not be interrupted by any recovery system upsets.

Advantages of the Water Recovery System.

The processes of the present invention provide several significant and unexpected advantages over conventional treatment processes including improved food safety and improved process economics. The invention, in a preferred embodiment, is designed to operate in a cascade type flow where water is recovered "downstream" from evisceration and carcass washing operations and is treated and then reused in "upstream operations" such as scalding, picking, stunning and flume type operations. Additionally, the treated water may be reused in chiller makeup operations, sanitation wash and other approved reuse applications. Avoidance of closed loop applications of reuse water is seen as both desirable and prudent for a number of reasons: 1) due to the inorganic species found in poultry process water (i.e., specifically high phosphorous levels and calcium from the processor's water supply) the potential for unwanted precipitation of calcium phosphate or, other deposits on poultry product or plant equipment can be mitigated, 2) the inherent food safety advantages in "cascading" reuse water to points not used in recovery mitigates the potential for cross contamination, and 3) avoidance of cycling up or, concentration of unwanted organic compounds such as ammonia and other organic nitrogen compounds that could potentially have a negative impact on product contact or, non-product contact applications.

In such situations, limiting the collected water for treatment to include ranges approximating from one (1) to about a ninety (90) percent chiller water is beneficial to prevent or limit the possibilities of contamination due to the above stated reasons. Further, limiting the collected water for treatment to approximately between twenty (20) and forty (40) percent has been found to be ideal, although higher percentages are clearly contemplated in this disclosure providing that the treated water meets the above stated criteria. Similarly, once the collected water has been treated and reintroduced into the processing steps, it is preferable to limit reuse of the treated water into the chilling steps to approximately between twenty (20) and forty (40) percent of the treated water although varying percentages are hereby contemplated in the present disclosure.

By focusing on the recovery of the carcass final wash stream, inside/outside carcass wash cabinets or other relatively low load source streams, the process becomes inherently safer due to the fact that this stream is not the result of a communal bath for animal carcasses. This improved microbiological safety occurs because communal baths create a substantial potential for cross contamination. For example, the presence of one carcass containing pathogens in a communal bath creates the potential opportunity to spread the pathogens to other non-infected carcasses in the communal bath. In addition, adding the pathogenic load to recovered process water adds to the challenge of disinfection of the recovered water and raises the risk of reintroducing such pathogens into other processing stages when the recovered process water is reused.

Accordingly, by avoiding exclusive reuse of the chiller bath water, using the process of the present invention, safety of the food product is enhanced because the water quality of the recovered carcass final rinse and other relatively low load source streams is significantly better than the quality of the water contained in the poultry chiller. This is in part due to the fact that the final wash water is in one-time contact with the final product and therefore has not had a long contact time with the food product to absorb into solution additional fats, oils and grease. Thus, by reusing downstream processing water and, more importantly, avoiding reuse of the upstream chiller water or water from an initial wash step, significant increased safety is imparted to the process.

Additional food safety benefits are offered by the invention due to the fact that advantageously dosed rechlorinated water is being returned to a number of "upstream operations" such as scalding, picking, stunning and flume type operations. In some cases the plant may not be regularly or adequately chlorinating the process water at these points of operation. The treated reuse water being directed to these reuse points is chlorinated at an advantageous dosage. It was surprisingly discovered that such advantageously dosed chlorinated reuse water is beneficial to the reduction in microorganisms on the carcasses being processed using said reuse water.

In a preferred embodiment and as will be apparent from the embodiments disclosed herein, the reuse water is chlorinated with an advantageous dosage of chlorine or other approved disinfectant and is reintroduced "upstream" such as in the scalder or similar heating portion of the processing steps. During the scalding or heating processing steps, the pores and tissue membranes of the carcasses are open and are more readily receiving of the surrounding water, i.e., the reintroduced chlorinated water. The reintroduction of the chlorinated reuse water into the scalder or similar heating processing step causes a dramatic reduction in the levels of microorganisms associated with the carcasses that has not been found in the prior art.

Additionally, by avoiding exclusive reuse of the chiller bath water, the relative economics become significantly more favorable to the end user due to the fact that later streams such as the final carcass stream contain significantly less contamination mass. Because the economics of treatment are largely dependent upon the mass of compounds to be removed, by significantly diluting any chiller water with water from other sources or by eliminating chiller water entirely, the contaminated load on the purification process is significantly lessened and with it the concomitant cost.

Recovery Sump

The present invention also provides a new methodology developed to recover poultry wash water from various stages of the product processing operations where water is captured from the wash or rinse cabinet(s). Such techniques are optionally employed in integrated water treatment systems directed at maximum recovery, treatment and reuse of such process water, such as that described herein. Such techniques are best employed in those plants where plant logistics are complex and plant trench drain systems are not available.

The device of the present invention allows for maximum removal of solid matter, floatable fats, oils, and grease, animal parts including skin, small body parts and detritus. The early removal of these constituents at or close to the source of the water from wash or rinse cabinets provides far greater efficiency and reduces significantly the complexity of treatment components in the later treatment stages of the integrated water recovery process. It was surprisingly discovered that by removing a greater mass of constituents at, or close to the recovery source, a greater impact on downstream water treatment economics was obtained.

A preferred embodiment is capable of collecting water from a typical poultry slaughter line wash station. A primary function of this apparatus is to provide a collection basin for the wastewater from the carcass wash cabinets and other source points. A secondary function of the apparatus is to provide for a hydraulic design that allows a continuous skimming of the floatable solids, fats, oils and grease that are the typical contaminants found in such waste streams. The apparatus also serves as the point where the water, after solids removal, is transferred from the processing floor to a treatment system located outside the processing facility for further treatment.

Figure 2:
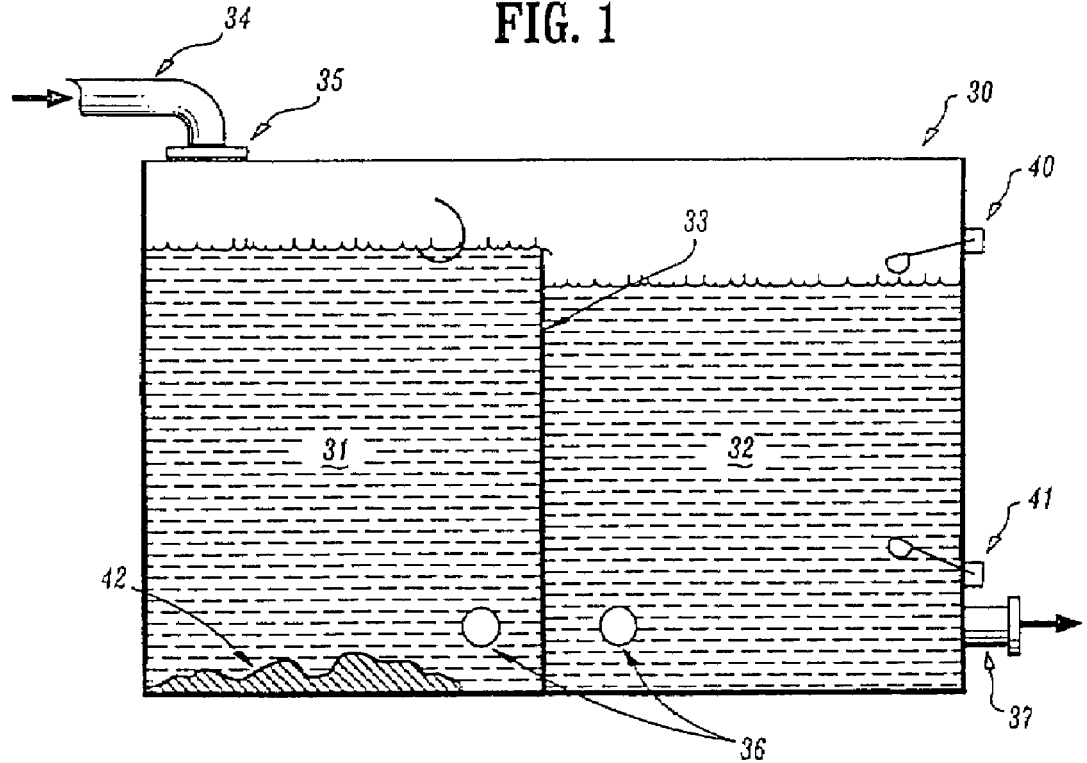
FIG. 2 is a side cross-sectional view illustrating the recovery sump device shown in FIG. 1.

In a preferred embodiment and with general reference to FIGS. 1 and 2, the device comprises a specially designed stainless steel sump containing floatation chambers, weirs, screens and clarified water flow channels. While the exact dimensions of this device can be advantageously varied from application to application, all such devices would ideally include most, if not all, of the following features: a main sump vessel, a screened top, overflow ports, weirs and slant plates, a deep sump, float sensors and a system transfer pump.

The apparatus comprises a rectangular, welded basin 30 of a size and volume to permit proper hydraulic flow and overflow for the specific waste streams to be collected and transferred.

The basin 30 is fitted with configured baffles 33 to separate the turbulent flow section 31 (associated with waste stream collection) from the relatively quiescent portion 32 from which the water may be pumped for further treatment. The number and configuration of the baffles is application specific and, to a large extent, will depend upon the volume of water to be collected and transferred.

The apparatus is also fitted with a skimming device 39 consisting of a "half-shell" stainless steel tube or weir pipe. The tube skimmer 39 is adjustable in its vertical orientation to allow for fine-tuning to the specific application intended. The number and location of these skimming tubes will also depend upon the volume of water and flow velocity for a specific application. The end of the weir pipe 38 communicates with a drain allowing removal of skimmed solids. The apparatus is also advantageously fitted with a mesh screen 35 located at inlet 34 to prevent the entry of large solids (animal parts, skin and other gross solid matter) from fouling or clogging the collection sump and attached piping.

To facilitate operation of the apparatus as an integral part of a wastewater treatment system, the device is also fitted with level sensors 40 and 41 to actuate the attached transfer pump (not shown) only when the desired water level is reached. The sensors also shut down the pump when the water level has fallen below the "low level" setting to prevent the pump from dry cycling which may cause damage to the motor and other components. The device is fitted with outlet fitting 37 to which the pump suction is attached to enable transfer of the collected, treated water and drain plugs 36 to allow for ease of cleaning during the plant's sanitation procedure and removal of collected solids 42. The materials of construction of basin 30 are ideally stainless steel in order to conform to the USDA criteria for food processing equipment.

Operation of the Water Recovery System

Figure 3:
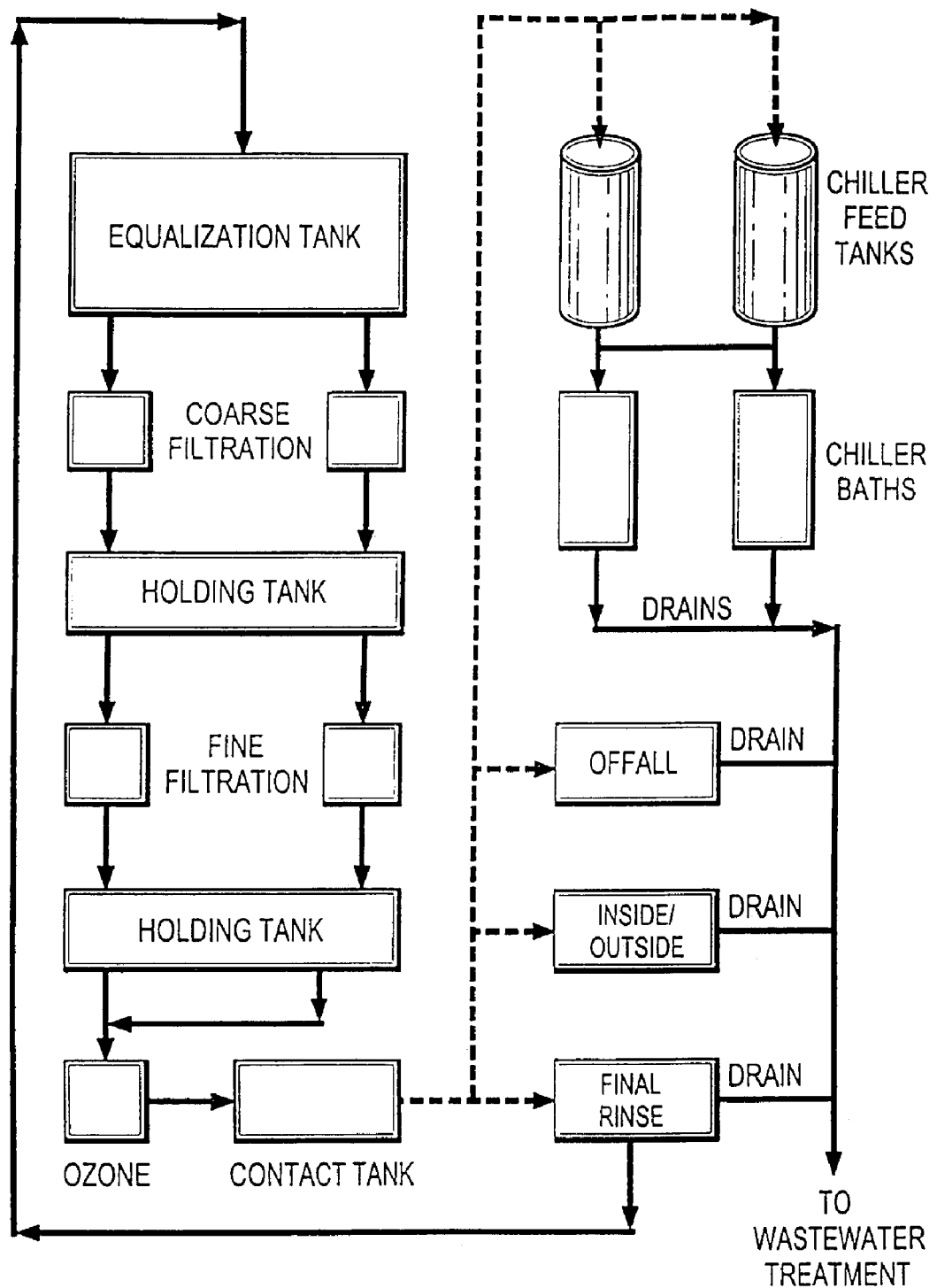
FIG. 3 illustrates an overall flow chart of one particular embodiment of a water recovery system, in accordance with the present disclosure.
Figure 4:
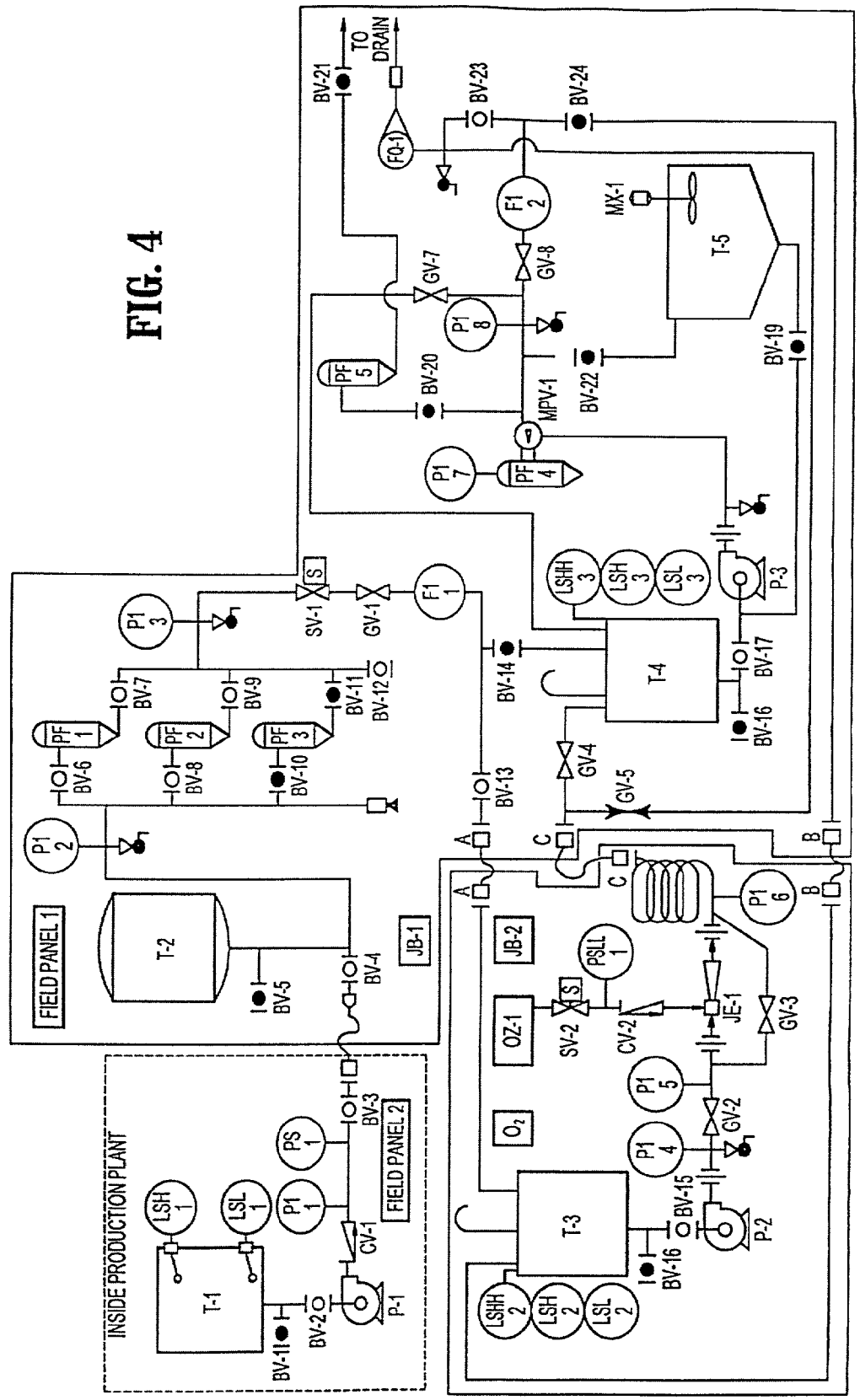
FIG. 4 illustrates an alternate embodiment of a detailed operative engaging flow plan.
Figure 5:
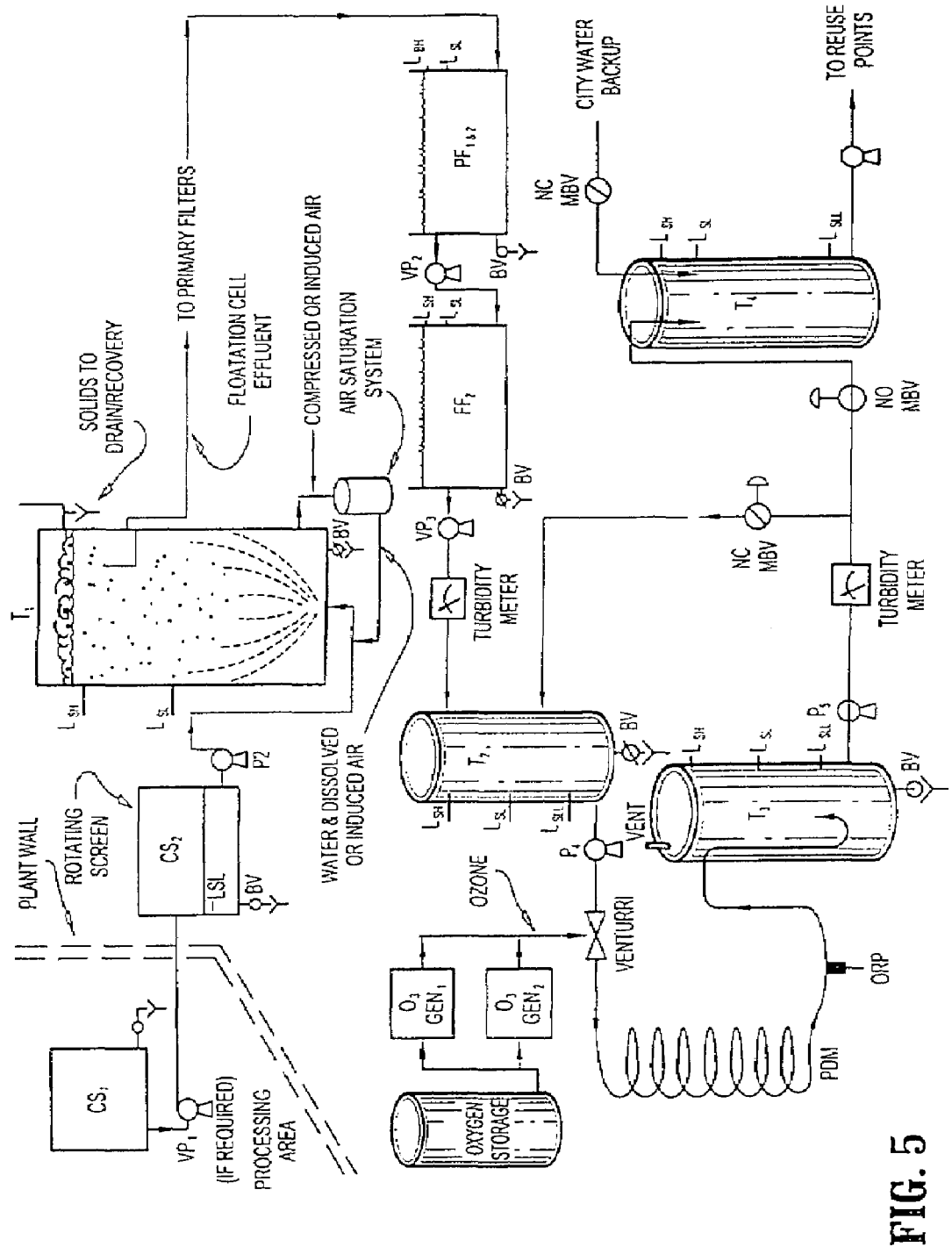
FIG. 5 illustrates a flow chart of another embodiment of the water recovery system according to the present disclosure.

With reference to FIGS. 3–5, the treatment process is designed to deliver a final quality of water that is safe for intended use as carcass or bird chiller makeup water, evisceration wash water, inside/outside wash water, sanitation cleanup water or use at any other point requiring a high quality, pathogen free, chlorinated wash or rinse water source. The present invention capitalizes on the discovery that the carcass washing in inside/outside carcass wash cabinets, "water rails," organ or paw transport flumes and final rinse stages represent the cleanest sources of potential reuse water available in high volume and that the treated water from the proposed treatment system will deliver water meeting the following quality standards (See, the Food Safety Inspection Service (FSIS) of the U.S. Department of Agriculture, FSIS Directive 11000.1, Water Supply and Water, Ice and Solutions Reuse, 9 CFR 416.2(g), as well as 40 CFR Part 141—National Primary Drinking Water Regulations):

1. Absence of pathogens (*E-Coli*, Fecal Coliform, Total Coliform, Aerobic Bacteria, *Salmonella*);
2. Turbidity no greater than 5 NTU's;
3. Treated water is safe for the intended use;
4. Total Plate Count is less than or equal to 500 CFU/ml; and
5. Chlorine Residual of greater than or equal to 1 PPM Free Chlorine.

In cases where the plant layout allows, the preferred method for capture and recovery of source water is accomplished by custom designed collection devices located in close proximity to the source and connected by means of piping to a common collection header installed in the plant's existing trench drain system. In cases where this is not possible, the recovery sump device (to be described later herein) is used as the initial collection point for source water.

The recovery sump device is ideally located under or adjacent to the poultry planes wash or rinse cabinets and is situated such that the wash or rinse water, after being sprayed (using typical spray nozzles) onto the animal carcass, is captured in the main sump. This water contains at this stage, high levels of solid materials including fat, skin, small animal parts, oils and grease as well as other organic and inorganic materials (contaminants) being washed off the carcass. The contaminant laden water then flows over and through the screened main sump top where gross solids are captured and allowed, by way of the angle of orientation, to be continuously washed off the recovery sump device into the plant's wastewater trough or piping. The water is then permitted to gravity flow over the recovery sump weirs which are fitted with channeling devices to promote the removal of "floatable" contaminants. Again, these contaminants are ideally removed from the device and flushed into the plant's wastewater drain system.

The device preferably contains float sensors; low level and high level, to activate the devices transfer pump. The level of water contained in the device will dictate when the device is in overflow mode. Overflow mode is the level where water containing the "floatable" contaminants is higher than the sump's overflow ports, which are sized to allow for large pieces of material to be efficiently floated out of the system. The overflow level also ensures that the water in the device has had sufficient residence time to allow for floatation of the "floatable" contaminants to reach the surface of the water. The device activates the transfer pump when the high level sensor indicates that the overflow mode has been achieved. The actual settings of these sensors are advantageously calibrated during installation of the device to allow for application specific conditions. The water captured in the device is flowed (by gravity) through a series of different vertical height weirs which act as the traps for solid, floatable contaminants. These weirs have flow channels in the bottom which allow for "clarified water" to flow. Each section of the device is designed to remove successively smaller (in mass) contaminant particles.

The collected water is then pumped by way of a vacuum type, pump(s) to the treatment system's common collection and rotary screening device for additional solids separation and removal ideally located outside of the main plant. The main influent/floatation tank ideally is fitted with dissolved air floatation or, induced air floatation which utilizes compressed air introduced into the floatation chamber by gas/liquid injection device(s) to promote flotation of suspended solid material (largely fats, oils, grease and animal matter). The skimmed product may be captured and recovered for rendering. This tank serves as the main reservoir and surge tank allowing for smoothing of volumetric flows during the plant's operations.

The treatment system comprises five major component arrays including source point collection/solid separation, primary screening, floatation/aeration, primary filtration, fine filtration and disinfection. The primary filtration module is comprised of either vacuum type, diatomaceous earth filtration vessel(s), electrocoagulation reactor(s) or membrane separation modules. The media used in these vessels can be standard, commercial grade diatomaceous earth, which is ideally "precoated" onto the vessel's stainless steel matrix septum.

The water is filtered to remove further organic content including fats, oils and grease. The primary filtration module can be recirculated at a higher rate than the process throughout to allow for multiple pass type filtration. The primary filtration modules can be operated in parallel or sequentially to promote maximum removal of solids, fats, oils and grease. This module can be configured with redundant (backup) module(s) that are ideally controlled by the systems main control panel. Such that, when the pressure differential exceeds the design parameters programmed into the control panel's programmable logic controller, an alarm is activated to notify the operator that the filtration module is approaching a fully loaded stage. The alarm will not shut down the system unless the on-line turbidimeter reaches a predetermined high level. The on-line turbidimeter can perform either system shutdown or, activation of a motorized ball valve to shunt the flow to the standby filtration module. The water from the primary filter module is then pumped to an intermediate tank (for example, 3000 gallons) where settling and equalization is accomplished and this tank serves as a smoothing station for the system to allow for a continuous, batch type operation.

Filtered water from the first intermediate-tank or alternately from the primary filtration module is pumped to the final polishing module by way of a centrifugal, end suction, top discharge type pump. The final filtration module comprises a vacuum type, diatomaceous earth filtration vessel and is precoated with a blend of standard commercial grade diatomaceous earth and an absorbent, cellulose type media. Alternative devices such as membrane separation devices or multi-media filtration modules may be employed where water quality dictates their efficacy.

The final polishing module is advantageously fitted with a Hach (or equivalent) on-line turbidimeter to continuously monitor the turbidity of the filtered water. These filters are designed to remove further organic material, fats, oils and grease. This module can be fitted with a backup module to allow for "hot" switching in the event that the pressure differential exceeds the programmed high level. The pressure/vacuum differential is monitored and will activate an alarm condition at a predetermined set point. Again, this alarm will not shut down the system unless other parameters are exceeded. The alarm is to notify the operator that the filters are reaching the loaded stage. Most preferably the final filtered water then enters a second intermediate tank, which serves as an equalization tank and settling basin, however, this step may be optionally eliminated.

The filtered water is then pumped by a centrifugal, end suction, top discharge pump to the disinfection system. Disinfection is accomplished by the introduction of gaseous ozone into the filtered water. Ozone is generated by a corona discharge type ozone machine using cryogenic oxygen or, oxygen separated by pressure swing adsorption on-site as the parent gas. The ozone is preferably introduced into the filtered water by way of a venturi type gas/liquid mixing device (Mazzei Injector). The ozonated water is pumped through a pressure dwell manifold or a high efficiency, centrifugal gas/liquid mixing device to promote maximum dissolution of the ozone gas. The ozonated water flows to an ozone contact tank (304 stainless steel) ideally sized to achieve a minimum of about 7 to 10 minutes contact time. Ozone generator sizing has been based on U.S. EPA criteria for 3 to 4 log removal efficiency at an applied dose of a maximum of 7 ppm and a standard of 5 ppm. The ozone contact tank is fitted with either a dissolved ozone measuring device or, an Oxidation-Reduction Potential (ORP) probe. This probe is interfaced with the dissolved ozone monitor or, ORP monitor in the system's main control panel and dissolved ozone level or, ORP is constantly displayed on the panel front. ORP and/or dissolved ozone is ideally controlled to achieve the desired disinfection standard determined by microbiological analysis at various dissolved ozone or, ORP set points to assure that the water is pathogen free. A 750-mv ORP set point is commonly used to indicate the sterility of water. The International Bottled Water Association (IBWA) and others state that, at this level of oxidation, the water is deemed sterile by drinking water standards and that microbiological activity is eliminated. An alarm is activated if dissolved ozone level or, ORP falls below the programmed setpoint and the system can be shut down.

The treated effluent from the system will then be advantageously piped to the plant's bird chiller storage tanks for use as bird chiller makeup or to additional reuse points including but not limited to the scalder, evisceration wash water, defeathering wash water, inside-outside carcass wash, and sanitation cleanup water to allow maximum volumetric reuse.

Control of the treatment system's operations is preferably accomplished by way of a Programmable Logic Controller (PLC). The Main Control Panel continuously monitors the treatment system's operations and performance using digital and analog inputs designed to monitor total volumetric flow (pulse type, digital flowmeter with totalizer), pressure differential sensors fitted to both primary filtration modules and final filtration modules, turbidity at effluent of primary filtration and at effluent of the ozone contact tank. An ambient ozone monitor is also preferably installed adjacent to the plant's bird chillers, or other acceptable reuse points, to continuously monitor ozone levels. All controls and safety devices are ideally interfaced with the main operating control panel and designed to notify the plant operator in the event of any system upset and interlock the system in the event that the final water quality fails to meet the standards established above.

Additional Reuse Water Quality Assurance & Safety Considerations

With particular reference to FIGS. 4 and 5, the treatment system is fitted with various monitoring and safety devices such as a solenoid shut-off valve fitted at the reuse water fill line to the bird chiller water storage tank. The solenoid valve is activated to close in the event that the water quality standard, ideally 5 NTU's Turbidity, is not met. The bird chiller water storage tank and/or the treatment system's final product storage tank is also fitted with a backflow prevention valve on the city water inlet pipe to prevent backflow of the treated reuse water into the main city water line. Secondly, each filtration module is fitted with pressure/vacuum differential sensors to continuously monitor the performance of filtration. Alarm indicator lights are fitted to the systems remote monitoring panel to enunciate alarm status when pressure/ vacuum differential readings are out of the prescribed ranges, when turbidity of primary filtration is out of range and for effluent turbidity in NTU's. The treatment system continuously monitors turbidity at the discharge to the bird chiller storage tanks or other designated reuse points and is interfaced with the main system control panel to shut down the system in the event the final quality exceeds 5 NTU's at which time, water from the treatment system can be recirculated within the treatment system or, diverted to the plant's main wastewater drain.

The key to FIG. 4, which depicts a conventional engineering flow chart of a preferred treatment process is:

| ID LABEL | DESCRIPTION |
| --- | --- |
| F1-1 & F1-2 | Flow Indicator |
| FQ-1 | Flow Totalizer |
| JE-1 | Jet Inductor |
| LSH-1 | Level Switch High |
| LSL-1 | Level Switch Low |
| LSHH-2 & LSHH-3 | Level Switch Hi-Hi |
| LSH-2 & LSH-3 | Level Switch High |
| LSL-2 & LSL-3 | Level Switch Low |
| MX-1 | Mixer |
| OZ-1 | Ozone Generator |
| P-1 thru P-3 | Centrifugal Pump |
| PF-1 & PF-2 | Particulate Filter |
| PF-3 | Particulate Filter |
| PF-4 | Particulate Filter |
| PF-5 | Particulate Filter |
| PI-1 thru PI-8 | Pressure Indicator |
| SV-1 | Solenoid Valve |
| SV-2 | Solenoid Valve |
| T-1 | Collection Tank |
| T-2 | Pressurized Tank |
| T-3 & T-4 | Surge Tank |
| T-5 | Slurry Tank |
| BV-# (black circle) | Motorized Ball Valve-normally closed |
| BV-# (open circle) | Motorized Ball Valve-normally open |

The ball valves are ideally controlled through the programmable processor control based on readings obtained from monitoring sensors and level switches. Control is designed to ensure adequate supplies of water at each stage of the system and that turbidity, NTU and microbiological load requirements are continuously met.

FIG. 5 depicts a flow chart of a preferred embodiment of the treatment process. In addition, FIG. 5, in comparison to the process shown in FIG. 2, demonstrates the advantageous flexibility inherent in the treatment and recovery process of the invention and the ability to use different components at certain stages of the process to accomplish desired goals. Still other substitutions can be made, such as using electrocoagulation to accomplish the filtration effected by diatomaceous earth filters.

The key to FIG. 5 is:

| ID LABEL | DESCRIPTION |
|---|---|
| P | Pump |
| CS | Collection Sump |
| VP | Vacuum Pump |
| T | Tank |
| LSL | Level Sensor Low |
| LSH | Level Sensor High |
| PF | Pre-Filter (diatomaceous earth) |
| MBV | Motorized Ball Valve |
| FF (1 & 2) | Final Filter |
| FF (3 & 4) | On-line Standby Final Filters Added as Needed |
| PDM | Pressure Dwell Manifold |
| O3 Gen (1 & 2) | Ozone Generators |
| BV | Ball Valve |
| LSLL | Level Sensor Low-Low |
| NC | Normally Closed |
| NO | Normally Open |

Additionally, the ozone disinfection module is continuously monitored using the ORP or, Dissolved Ozone ($DO_3$) probe and monitor. A low ORP or ($DO_3$) alarm is enunciated on the remote monitoring panel to indicate system fault should the ORP/$DO_3$ fall below the site-specific ORP/$DO_3$ level. The ORP/$DO_3$ monitor and controller will immediately shut down the system in the event that ORP/$DO_3$ falls below site specific low level ORP/$DO_3$ reading and the system will be placed in alarm shutdown mode. Further, an ambient Ozone Monitor is installed adjacent to the two bird chiller baths, or other acceptable reuse points, within the plant to continuously monitor ozone levels.

The Ozone Monitor will announce ambient levels above 0.06 ppm and activate system shutdown at a level exceeding 0.08 ppm to assure compliance with OSHA standards. Also, the treated reuse water entering the facility shall be free from ozone residual to prevent contact of product with a non-approved substance. This may be advantageously accomplished by providing sufficient residence time in transit to and storage in the treatment system's final storage tanks to allow for complete dissipation of ozone. Alternative techniques employing ultraviolet radiation or, activated carbon adsorption may be used where final ozone concentrations are detected to be high. In this regard, it is useful to note the half-life of ozone is approximately 5–15 minutes in aqueous solution.

The treatment system according to the present disclosure is designed to be operated continuously during the plant's processing operations and the system is ideally designed to undergo sanitation during the plant's sanitation shift. To ensure integrity of the system, all piping from the system's collection devices will be labeled clearly as "REUSE WATER" for ease of identification, and all materials of construction and media coming in contact with the recovered water have been selected to comply with FSIS Food Safety Standards. With the exception of the system's recovery and collection devices and in-plant piping to the treatment system, components are advantageously located outside of the processing facility.

In the embodiments of the treatment systems and methods described above, there have been found unexpected results as a consequence of operating experience with the present disclosure. By focusing on cleaner sources of water primarily from non-chilling steps with lighter organic loads the treatment processes of the system described are less expensive and more economically viable than systems described by others. Carcasses processed with reuse water from a system produced by the teachings of this invention have significantly less potential to be adulterated with precipitated inorganic or organic material, avoiding precipitation of such materials on poultry carcasses or processing equipment if reuse water is cycled too many times. A water reuse system that meets or exceeds food safety and regulatory guidelines adds economic value to the poultry processor. The results of using such reclaimed and properly treated water is further observed in the reduction of pathogens found on the carcass after evisceration and chilling. The reduction in pathogens is an important step in food safety, and has direct impact on liability in consumer safety.

Further, while some of the major benefits of the system is the conservation of large volumes of water and reduction of pathogens, a number of additional food safety and quality benefits are readily apparent. Such benefits and results include a significant improvement in the "picking" and "scalding" operations by the addition of the treated and recycled water to the pickers and scalders, that is, the point in the processing where the feathers are removed from the carcasses. By the addition of the treated and recycled water to the Pickers and Scalders, the overall effectiveness of the scalding and picking operations have been improved dramatically.

In addition to a reduction in microorganisms in the process, the pigmentation of the carcasses has not been effected, i.e., the color of the carcasses is more "yellow," which is preferred since it can result in the processor getting a higher price for the carcasses (i.e., skin esthetics). Also, the carcasses are retaining more of their natural fat which means a higher weight per carcass which translates directly to higher prices per carcass.

The reuse process involves the segregated recovery of specific water streams used in the evisceration and chilling processes and then treatment via a proprietary process of screening, floatation, filtration, ozonation and chlorination. The process produces the product that is allowed by the USDA for return to poultry processing plant for product contact. When such water is used as replacement source water in the scalding and picking operations, efficiency of defeathering operation is significantly enhanced to the point of being a preferred method by such processing plants.

The driver for the improved scalding and picking operation is attributed to two factors. First, the reaction of ozone with animal fats, generally known as fats, oils, grease and/or lipids, will produce specific surface-active agents and surfactants that cause a reduction in surface tension of the water (recovered, reuse or otherwise), and thus improved contact of the heated water on the oily skin of the poultry or carcass. This, in turn, allows for better release of the feathers and thus improved removal of the feathers in the picking operation. Processing plants using this process have testified to dramatically improved efficiency in feather removal, fat retention and desired skin esthetics.

It is also contemplated within the present disclosure that a separate surfactant or surface-active substance may be added to water used with any of the poultry processing steps. The addition of the separate surfactant or surface-active substance will also reduce the surface tension of the water which enhances the ability of the water to infiltrate the pores and skin membranes of the poultry. Surfactants or surface-active substances are known outside the food processing arts. Those surfactants or surface-active substances which may be readily and safely used with the processing of foodstuffs are expressly contemplated by the present disclosure.

The reactions of ozone and chlorine with water being treated for reuse generates hypochlorous acid and/or other effective biocides. Ozone and chlorine also react with animal fats, generally known as fats, oils, greases, and/or lipids, etc., dissolved or contained in the reuse water, to produce specific surface-active agents and surfactants which reduce the surface tension of the water which it is dissolved. The combination of these specific surface-active agents and surfactants and effective biocides causes the release and destruction of bacteria from the poultry carcass. The specific reuse waters are recovered and treated before being returned to the scalders and pickers. The treatment protocol includes the filtration to less than (5) five NTU's, the ozonation to an ORP of 300 to 800 millivolts, and a chlorine residual of 1–5 mg/l.

Figure 6:
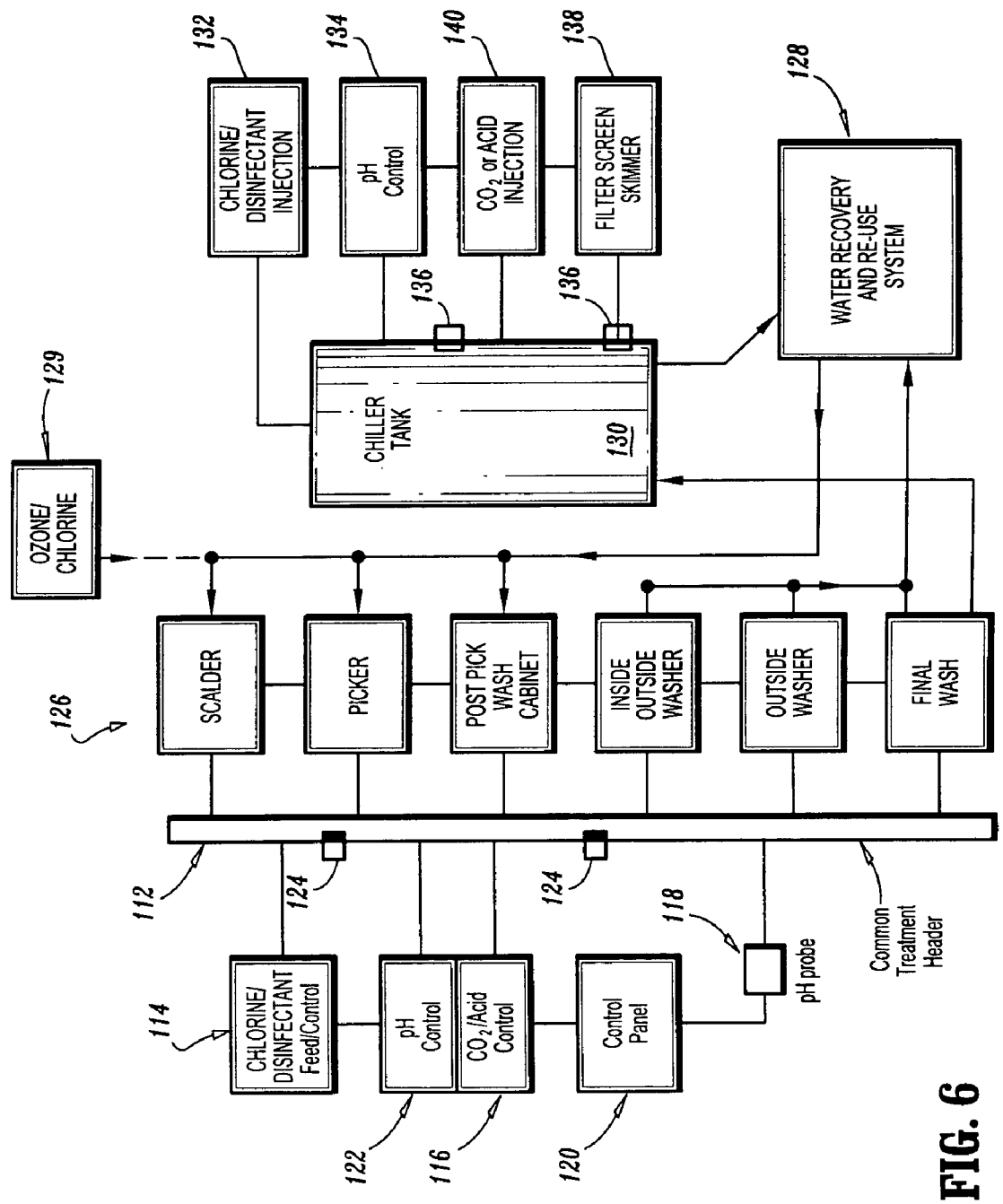
FIG. 6 illustrates a flow chart of a multi-stage chlorination process and chiller treatment system.
Figure 7:
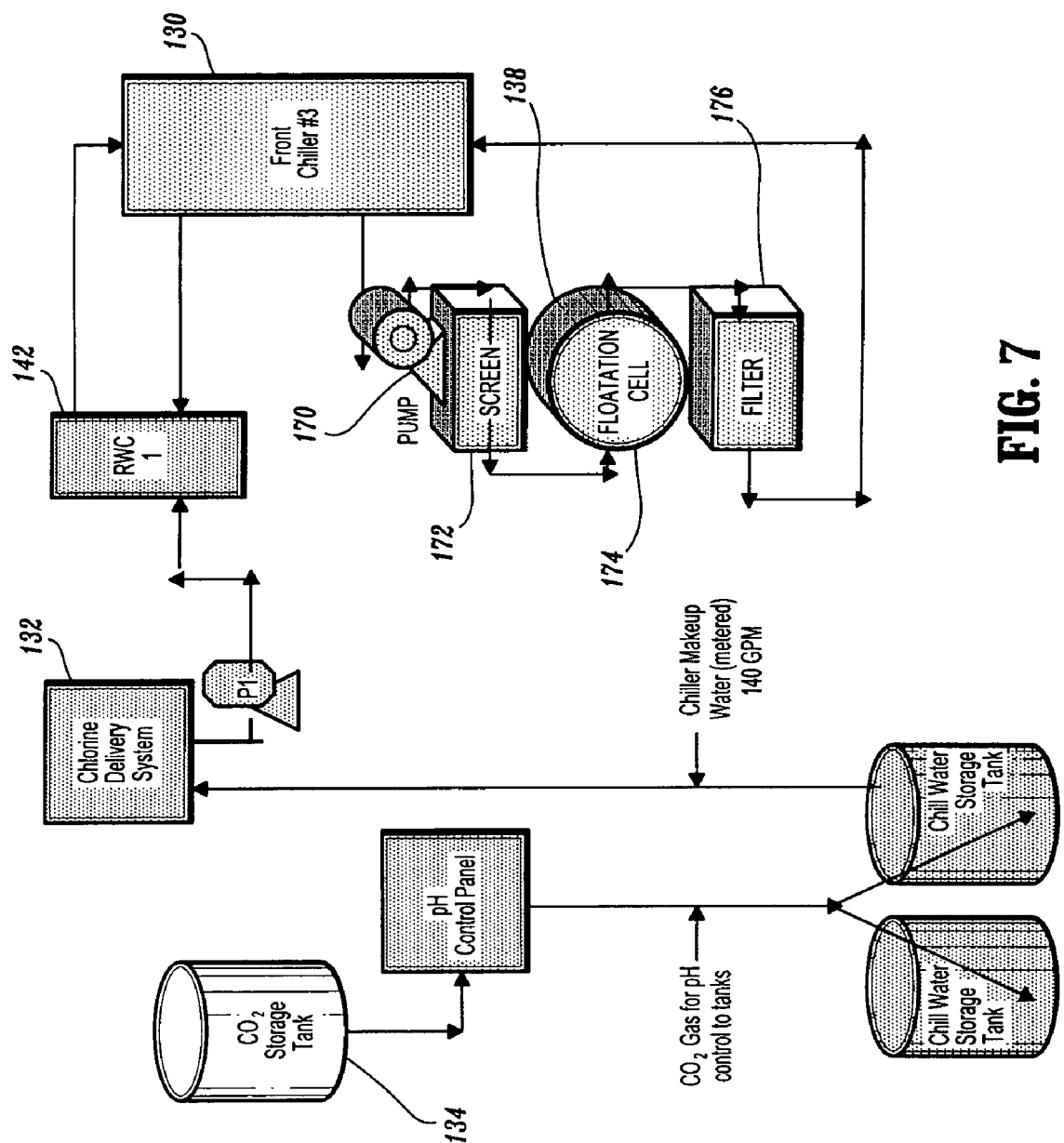
FIG. 7 illustrates an alternate embodiment of the chiller treatment system shown in FIG. 6.

Referring to FIGS. 6–7, another alternate embodiment is shown in accordance with the present disclosure, whereby the control of the pH of the treatment water within product processing water optimizes the elimination of pathogens and other microorganisms. Also, by providing an intervention step to allow for continuous on-line processing of poultry carcasses, there is a reduction in the amount of physical handling of carcasses and therefore, a reduction in the potential for cross-contamination of the carcasses, thereby improving quality and food safety. The present disclosure also discloses methods and devices for improving the effectiveness of disinfection agents in chiller tank processing water by substantial removal of filterable materials. A particular advantage is the fact that the methods of the present invention can be "retrofitted" to existing processing plants without any significant alteration of the plant's "footprint" or layout.

While the processes and devices described will be equally applicable to the aqueous processing of a variety of foodstuffs, for convenience, the application to the poultry processing industry will be described. This industry uses significant volumes of water in its processing operations. Much of the water used during such processing is regulated by the USDA, although the quantity and process steps vary from plant to plant. On average, the typical slaughter plant will use between 5 and 15 gallons per animal, divided into several key elements:

The Scalding process—USDA guidelines dictate a minimum of 1 quart per animal.

The Picking (de-feathering) process—varies from plant to plant.

The Evisceration process—varies from plant to plant.

Carcass washing (including Inside/Outside Carcass Washers, Intermediate Wash Stations and Final Rinse Cabinets)—these combined carcass wash steps can use between 2 and 6 gallons per animal.

The Chilling process (chillers)—USDA guidelines require minimum overflow rates of 0.5 gallons per animal in whole bird chiller tanks and temperature control. Various processors also utilize chilled water for "paws," gizzards and other edible organs sold commercially. Typical chiller operations can consume between 0.75 and 1.5 gallons per animal.

Plant Sanitation—plant sanitation can use between 1.5 and 3 gallons per animal.

Equipment wash—a typical processing plant will use between 0.25 and 1 gallon per animal in equipment washing (this is an "on-line" process and should be differentiated from sanitation during which the entire plant and equipment is washed and sanitized when the plant is not in production).

Miscellaneous water usage—truck wash, live loading shed wash, domestic water, wastewater and industrial (non-product contact uses such as evaporative cooling for refrigeration, vacuum pump seal and cooling and compressor cooling) wash.

Most of the water is used during the evisceration and carcass washing steps and is typically applied by mechanical mechanisms comprising spray washing devices, cabinet type washers, brush washers and medium and/or high-pressure water spraying heads. The present invention takes advantage of the use of these existing water processing steps and mechanisms in improving the disinfection of the processing water and thus the processed foodstuff thereby improving its quality and safety.

Figure 6A:
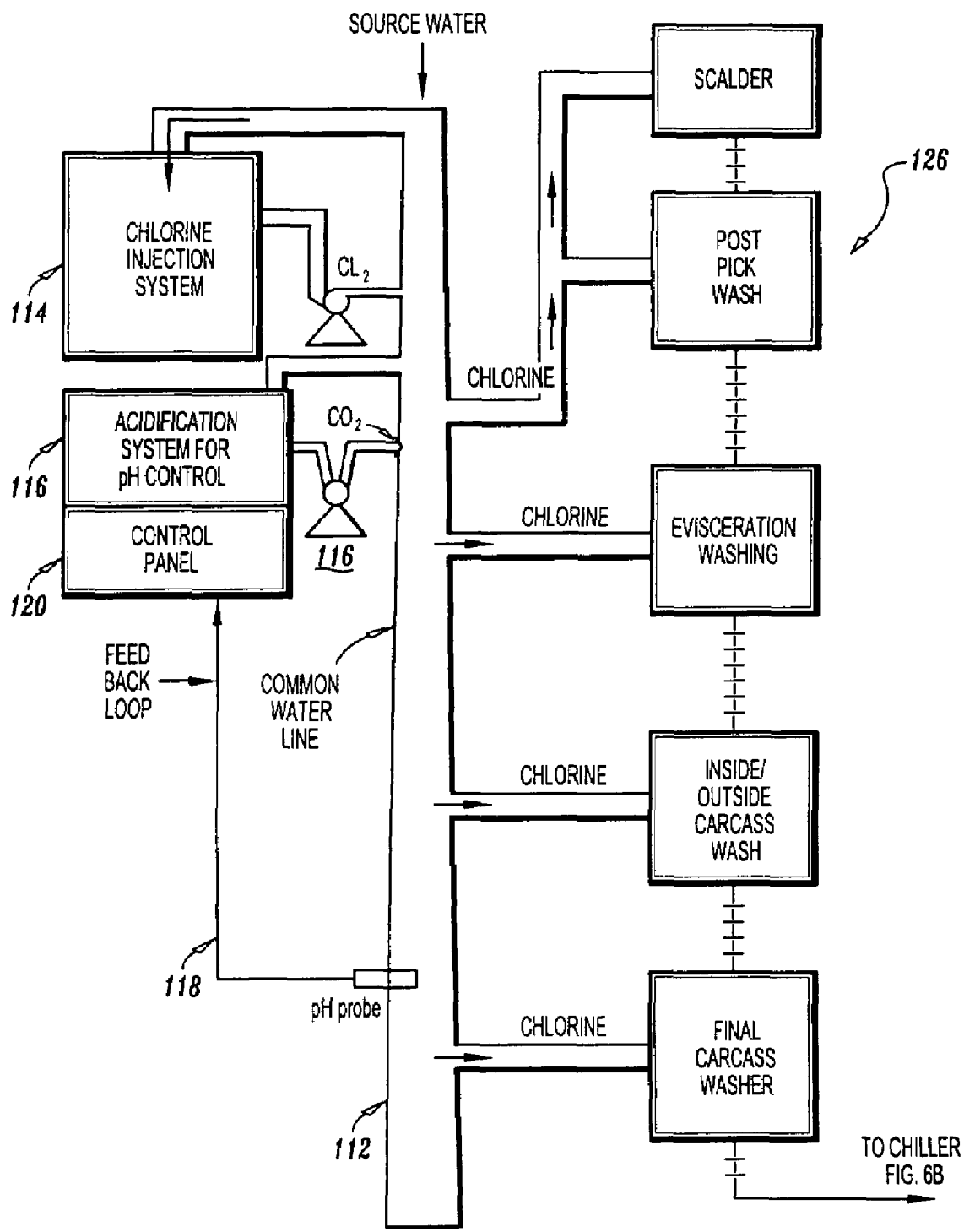
FIG. 6A illustrates a detailed flow plan of the multi-stage chlorination process shown in FIG. 6.
Figure 6B:
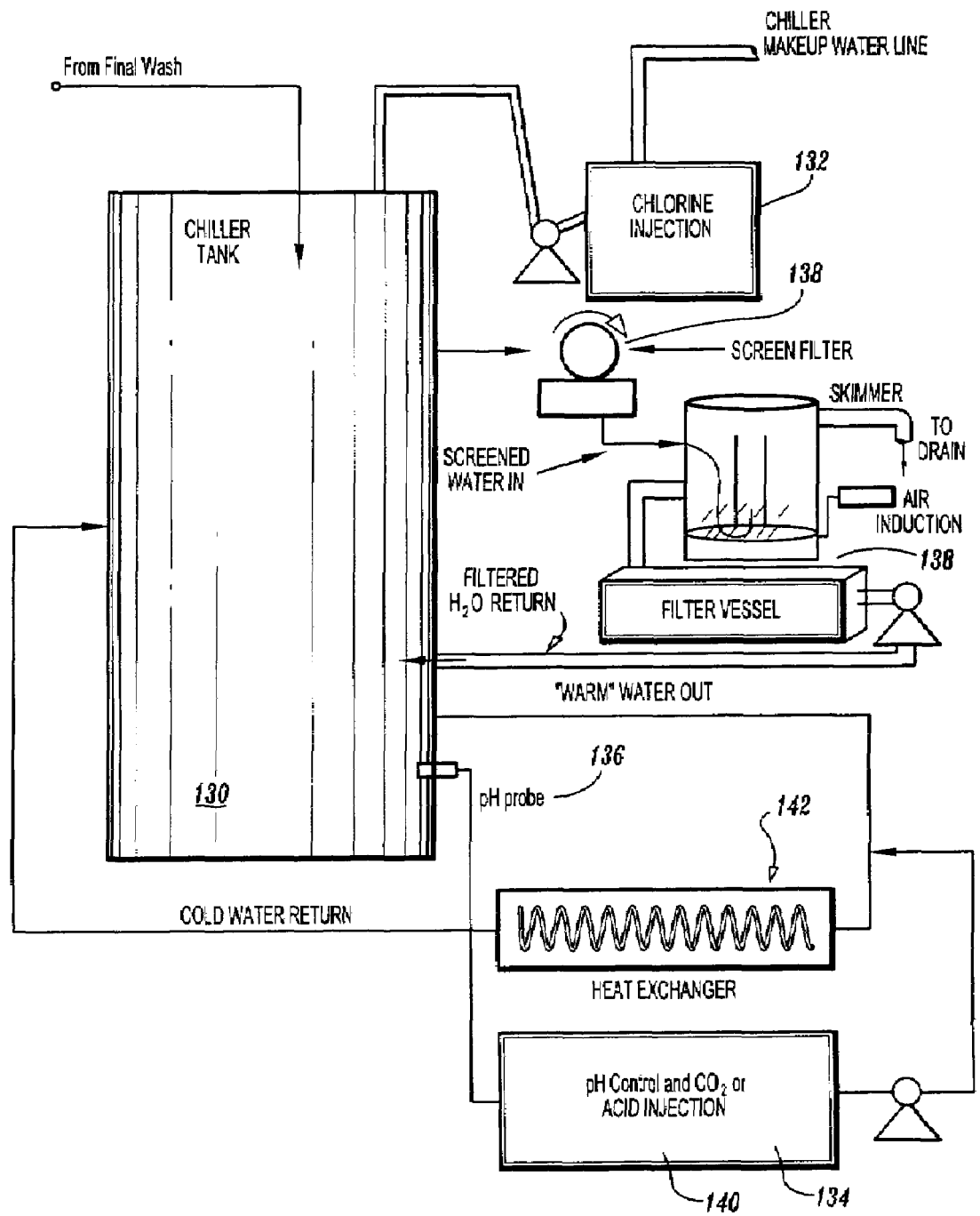
FIG. 6B illustrates a detailed flow plan of the chiller treatment system shown in FIG. 6.

Referring to FIGS. 6, 6A and 6B, the physical aspects of the present disclosure are illustrated as a common header 112 (either existing in the processing plant or, modification of the plant's water delivery system or, a custom, site built common header) used as the delivery mechanism to convey the treated water (e.g., calcium hypochlorite plus pH control) to the designated treatment points in the process. A tablet or liquid chlorine feed system 114 sized to deliver the maximum practical and allowable dosage of chlorine to the entire volume of water required to serve the multiple stages of treatment is situated along the common header 112. Also situated is a gas/liquid or, liquid/liquid injection device 116 to permit the introduction of the preferred acidification agent (e.g., $CO_2$, or other chemical agent) into the water in the delivery header to alter the levels of pH in the treatment water based on the readings of the pH probe 118. A control panel 120 is used along the process in order to monitor the readings and control the dosages of the chemical agents required to perform the disinfection and pH control 122. Multiple sensors 124 are located along the common header 112 in order to monitor, control the conveyance of the enhanced disinfection chemistry, measure chlorine levels and pH levels and send via electronic signal (feedback loops) the measurements to the proper chemical controllers.

The present disclosure makes use of (with or, without modifications) the plant's existing carcass wash cabinets and mechanical washing devices 126 to assist in the removal of visible contamination and serve as treatment points for the delivery of the enhanced disinfection chemistry. Devices for scalding, feather picking, post-pick washing and evisceration line washing stations act as additional treatment points for the delivery of the enhanced disinfection chemistry, as well as the plant's water recycle and reuse system 128, where the water has been disinfected with ozone (ozonated) or other appropriate disinfectant and then dosed with an appropriate level of an approved disinfection agent (e.g., calcium hypochlorite or others) before being reintroduced into the production process at an upstream point, such as in the scalder or similar heating portion of the processing steps. An alternative to the disclosed water recovery and reuse system 128 is an ozonating or chlorinating system 129 which simply ozonates or chlorinates outside water and reintroduces such water to any or all of the heated processing steps, i.e. the scalder step, the picker step and the post-pick step, which utilize heated water (heated water being defined as water used during poultry processing which is or was heated at some point, preferably, but not limited to, at the scalder step). This reintroduction, like with the water recovery and reuse system 128, reduces the levels of contamination within the poultry.

Multi-stage, Controlled pH Chlorination During Poultry Processing

While the USDA mandates the use of a disinfection agent (typically chlorine) at various stages of the poultry processing operations, it is silent concerning the conditions under which the disinfection agent is employed. It has been discovered that the effectiveness of the disinfection agent may be dramatically altered by characteristics of the processing water being treated, most notably pH, but also by the solute load presented by filterable materials. Other aspects of the present invention lie in the ability to improve the disinfection quality of the processing water at multiple points during processing. This becomes important because the effectiveness of a disinfection agent is directly proportional to the time in which the microorganisms to be killed are in contact therewith. The importance of contact time has been reflected in the US Environmental Protection Agency's (USEPA) Contact Time "CT" Values, in its guidelines concerning the disinfection of drinking water. These relationships have been perhaps most clearly spelled out by a mathematical formula developed by Chick in 1908, which described the kinetics of disinfection:

$$N_t = N_0 \exp(-kt)$$

Where:

$N_t$=number of microorganisms surviving after time t $N_0$=initial number of microorganisms $-k$=rate constant dependent upon type of microorganism and disinfectant t=time the organisms is in contact with the disinfectant USEPA CT Values are expressed as mg/L-min; where mg/L=concentration of disinfectant min=time in contact with disinfectant Clearly then, the longer and/or more often that the microorganisms (whether in the water or on the poultry being processed) come into contact with the disinfectant, the greater the reduction of microorganisms and the safer the poultry.

However, it has been discovered that there are still other factors which must be considered, including those which affect the efficacy of the disinfection agent. Several of the embodiments of the present invention take advantage of methods of optimizing these factors, chief amongst which is pH. The temperature and pH level of the water into which the disinfection agent, e.g. chlorine, is introduced can dramatically affect the effectiveness of the disinfection agent. This is illustrated by Tables 1–7 shown below, which are published by the USEPA concerning guidelines to CT values (lower numbers mean higher antimicrobial efficacy) in drinking water. These tables show the dramatic improvement in effectiveness of chlorine and chlorine derivatives at both lower pH and higher temperature. The tables also demonstrate how different microorganisms react differently to disinfection agents, e.g., viruses require longer contact periods to be inactivated.

The methods of the present invention capitalize upon these effects by adjusting the pH of the processing water to levels between pH 5 and 8, most preferably between pH 6.5 and 7, and by bringing such pH controlled disinfecting water into contact with the carcasses at multiple processing points. While the level of hypochlorous acid will continue to increase as pH levels continue to decline (thereby resulting in greater anti-microbial activity), the resulting corrosive nature of liquids with severely depressed pH can have deleterious effects upon plant equipment, not to mention hazard to equipment operators and hence, such reduced pH levels do not represent the optimum practical levels. The inverse of this is also true.

TABLE 1

CT Values for 3-log (99.9%) Inactivation of Giardia Cysts By Free Chlorine at Water Temperature 10.0° C. (50° F.)
Free Residual, mg/L

| | pH | | | | | | |
|---|---|---|---|---|---|---|---|
| | ≦6.0 | 6.5 | 7.0 | 7.5 | 8.0 | 8.5 | ≦9.0 |
| ≦0.4 | 73 | 88 | 104 | 125 | 149 | 177 | 209 |
| 0.6 | 75 | 90 | 107 | 128 | 153 | 183 | 218 |
| 0.8 | 78 | 92 | 110 | 131 | 158 | 189 | 226 |
| 1.0 | 79 | 94 | 112 | 134 | 162 | 195 | 234 |
| 1.2 | 80 | 95 | 114 | 137 | 168 | 200 | 240 |
| 1.4 | 82 | 98 | 116 | 140 | 170 | 206 | 247 |
| 1.6 | 83 | 99 | 119 | 144 | 174 | 211 | 253 |
| 1.8 | 88 | 101 | 122 | 147 | 179 | 215 | 259 |
| 2.0 | 87 | 104 | 124 | 150 | 182 | 221 | 265 |
| 2.2 | 89 | 105 | 127 | 153 | 186 | 225 | 271 |
| 2.4 | 90 | 107 | 129 | 157 | 190 | 230 | 276 |
| 2.6 | 92 | 110 | 131 | 160 | 194 | 234 | 281 |
| 2.8 | 93 | 111 | 134 | 163 | 197 | 239 | 287 |
| 3.0 | 95 | 113 | 137 | 166 | 201 | 243 | 292 |

TABLE 2

CT Values for Inactivation of Viruses By Free Chlorine

| | Log Inactivation | | | | | |
|---|---|---|---|---|---|---|
| Temperature, | 2.0-log | | 3.0-log | | 4.0-log | |
| ° C. | pH 6–9 | pH 10 | pH 6–9 | pH 10 | pH 6–9 | pH 10 |
| 0.5 | 6 | 45 | 9 | 66 | 12 | 90 |
| 5 | 4 | 30 | 6 | 44 | 8 | 60 |
| 10 | 3 | 22 | 4 | 33 | 6 | 45 |
| 15 | 2 | 15 | 3 | 22 | 4 | 30 |
| 20 | 1 | 11 | 2 | 16 | 3 | 22 |
| 25 | 1 | 7 | 1 | 11 | 2 | 15 |

Note: CT values can be adjusted to other temperatures by doubling the CT for each 10° C. drop in temperature.

TABLE 3

CT Values for Inactivation of Giardia Cysts By Chloramine Within the pH Range 6 to 9

| | Temperature, ° C. | | | | | |
|---|---|---|---|---|---|---|
| Inactivation | ≦1 | 5 | 10 | 15 | 20 | 25 |
| 0.5-log | 635 | 365 | 310 | 250 | 185 | 125 |
| 1-log | 1270 | 735 | 615 | 500 | 370 | 250 |
| 1.5-log | 1900 | 1100 | 930 | 750 | 550 | 375 |
| 2-log | 2535 | 1470 | 1230 | 1000 | 735 | 500 |
| 2.5-log | 3170 | 1830 | 1540 | 1250 | 915 | 625 |
| 3-log | 3800 | 2200 | 1850 | 1500 | 1100 | 750 |

TABLE 4

CT Values for Inactivation of Viruses By Chloramine*

| | Temperature, ° C. | | | | | |
|---|---|---|---|---|---|---|
| Inactivation | ≦1 | 5 | 10 | 15 | 20 | 25 |
| 2-log | 1243 | 857 | 643 | 428 | 321 | 214 |
| 3-log | 2063 | 1423 | 1067 | 712 | 534 | 356 |
| 4-log | 2883 | 1988 | 1491 | 994 | 746 | 497 |

*This table applies for systems using combined chlorine where chlorine is added prior to ammonia in the treatment sequence.

TABLE 5

CT Values for Inactivation of Giardia Cysts
By Chlorine Dioxide Within the
pH Range 6 to 9

| | Temperature, ° C. | | | | | |
|---|---|---|---|---|---|---|
| Inactivation | ≦1 | 5 | 10 | 15 | 20 | 25 |
| 0.5-log | 10 | 4.3 | 4.0 | 3.2 | 2.5 | 2.0 |
| 1-log | 21 | 8.7 | 7.7 | 6.3 | 5.0 | 3.7 |
| 1.5-log | 32 | 13.0 | 12.0 | 10.0 | 7.5 | 5.5 |
| 2-log | 42 | 17.0 | 15.0 | 13.0 | 10.0 | 7.3 |
| 2.5-log | 52 | 22.0 | 19.0 | 16.0 | 13.0 | 9.0 |
| 3-log | 63 | 26.0 | 23.0 | 19.0 | 15.0 | 11.0 |

TABLE 6

CT Values for Inactivation of Giardia Cysts
By Chloride Dioxide Within the
pH Range 6 to 9

| | Temperature, ° C. | | | | | |
|---|---|---|---|---|---|---|
| Inactivation | ≦1 | 5 | 10 | 15 | 20 | 25 |
| 0.5-log | 10 | 4.3 | 4.0 | 3.2 | 2.5 | 2.0 |
| 1-log | 21 | 8.7 | 7.7 | 6.3 | 5.0 | 3.7 |
| 1.5-log | 32 | 13.0 | 12.0 | 10.0 | 7.5 | 5.5 |
| 2-log | 42 | 17.0 | 15.0 | 13.0 | 10.0 | 7.3 |
| 2.5-log | 52 | 22.0 | 19.0 | 16.0 | 13.0 | 9.0 |
| 3-log | 63 | 26.0 | 23.0 | 19.0 | 15.0 | 11.0 |

TABLE 7

CT Values for Inactivation of Viruses by
Chorine Dioxide Within the
pH Range 6 to 9

| | Temperature, ° C. | | | | | |
|---|---|---|---|---|---|---|
| Inactivation | ≦1 | 5 | 10 | 15 | 20 | 25 |
| 2-log | 8.4 | 5.6 | 4.2 | 2.8 | 2.1 | 1.4 |
| 3-log | 25.6 | 17.1 | 12.8 | 8.6 | 6.4 | 4.3 |
| 4-log | 50.1 | 33.4 | 25.1 | 16.7 | 12.5 | 8.4 |

Accordingly, the preferred methods of the present invention incorporate the introduction of chlorine, a chlorine derivative (a preferred disinfectant agent), ozone or other approved disinfectant at a controlled pH (adjusted appropriately for the disinfectant employed given the additional practical considerations previously described). The introduction of such disinfectant in a combined system of chlorine injection (or mixing) and acidification (using carbon dioxide, citric acid, lactic acid or any other acid compound(s) approved for contact with food products by the USDA) into solution of the feed water is used in the following processing stages: the Scalders, the Pickers, the Post pick washers, the Inside Carcass Washers, the Inside/Outside Carcass Washers, the Outside Carcass Washers, the Final Carcass Washers and any other practical stage where water is used to physically remove contamination.

Similarly, disinfection of the foodstuffs are realized from the production of "chloramines" during the "up stream" introduction of the treated reuse water into processes employing elevated water temperatures. According to the present disclosure, the water reuse system incorporated in a poultry processing plant does not remove significant levels of nitrogen or ammonia from the process water which, subsequent to the ozonating step, combines with added chlorine passing through the cascade process, i.e., the gathering of process water from a number of source points in the production line, thereby forming various "chloramines" which, in the environment of elevated temperatures, aides in the reduction of microorganisms in the foodstuffs.

The processes of the present invention take advantage of frequent surface and internal contact of the disinfectant with the carcass to increase microorganism lethality and the disinfectant remaining on the carcass' external surface and internal surfaces to allow for additional time between the various process stages. Therefore, by beginning the treatment or disinfection process at earlier stages of poultry carcass processing, many advantages are realized.

First, introducing disinfectant at earlier stages results in inactivation (kill) of additional potentially pathogenic organisms not addressed in the current practices. The carcass will be at a higher temperature directly after the scalder stage and into the "post pick" stage. Higher carcass temperatures result in opening of the pores on the carcass skin and loosening of the skin from the muscle tissue. At these conditions, the disinfectant will contact surfaces and tissues that later become unavailable (e.g. closed) as the carcass temperature falls (especially in the chiller tanks).

Second, introduction of disinfectant during evisceration, the disinfectant will contact the surfaces of the carcass at the stage when potential contamination with fecal material or ingesta is most likely. Additionally, some residual disinfectant will be carried over to the next stage allowing for additional contact time.

Third, carcass washing with water treated with disinfectant, whether carried out in one stage or in multiple stages (various processors utilize different methods, washer designs and frequency of washers), will again allow for additional surface contact with the disinfectant at its highest efficiency (due to controlled pH).

Lastly, the entire process at these stages is also designed to reduce the contaminant (microorganism) load as the carcass is sent to the chillers. Any reduction in the organic loading prior to the carcass entry into the chiller tank will serve to reduce the risk of cross-contamination when the carcasses are immersed in a common tank (communal bath).

Enhanced Disinfection of Carcasses in Poultry Chiller Tanks

In an alternative embodiment, there is incorporated some of the same disinfection enhancements, as previously described, i.e., introduction of the disinfectant at pH levels where the maximum "active" compound is present in the poultry chiller tanks. Current practices and USDA guidelines require chiller tanks to be monitored for chlorine residual or total chlorine. The concentrations and testing protocols required vary from plant to plant. Generally because there are no specific mandates for disinfection of chiller tanks, there tends to be no uniformity in approach. The processes of the present invention benefit from utilization of an equipment package designed to continuously monitor and adjust the introduction of acidification to control pH level in the chiller tank as to allow for the maximum potential effective formation of hypochlorous acid (in those circumstances where chlorine is used) to enhance the disinfection process.

Similar practical considerations apply with respect to heat and the disinfection process. The invention is advantageously designed to utilize the elevation in water temperature at the scalding stage of the slaughter process. In poultry scalders, as well as the poultry picker and post-pick steps, the temperature of the water (and hence the poultry contained therein) is elevated to between 140 degrees F. and 170 degrees F. At these temperatures, the animal's skin releases from the muscle tissue and allows the aqueous chlorination to contact a larger surface area of the carcass. Also, the elevated temperature results in a higher reaction rate of chlorine reaction. Accordingly, the methods of the present invention, which provide controlled dosing of a disinfection agent, ideally will apply beginning with those processing steps which follow the initial slaughter steps.

With reference to FIGS. 6A and 6B, an advantage of the present invention includes the employment of a chiller tank water quality enhancement process. This process is ideally designed to continuously remove "filterable materials" from the chiller tank including FOG, TSS and COD. Disinfection is commonly affected by an oxidation process where the oxidant (e.g., hypochlorous acid, hypobromous acid, chlorine dioxide, ozone, hydrogen peroxide etc.) is the active disinfection agent. Since the oxidative reaction by the oxidation agent in water is a non-preferential one, the presence of high organic loading will pose a correspondingly higher oxidant demand to achieve comparable inactivation of microorganisms. To improve efficiency, the present inventive methods remove organics such as FOG, TSS and COD from the water to permit use of a lower disinfectant dosage to achieve the desired disinfection standard or "kill efficiency."

These methods can ideally be practiced with the preferred devices of the present invention which comprise mechanism(s) for continuous "mass load" organic removal. This is ideally accomplished by the use of mass removal by floatation, screening or other suitable means, followed by fine filtration using Diatomaceous Earth (DE) filters, membranes or other suitable methods of removing the identified "filterable" materials. It has been discovered that this will enhance the chiller tank's water quality, reduce significantly the disinfectant demand and greatly increase the efficiency of employing disinfection at this critical stage of the process.

The ideal process utilizes an equipment package designed to continuously monitor and adjust the introduction of acidification to control pH in the chiller tanks, and allows for the maximum potential effective formation of hypochlorous acid (where chlorine is used) to enhance the disinfection process. As previously described, the chiller water treatment equipment consists of similar equipment packages.

Using the USEPA CT values, this stage represents the highest potential for disinfection enhancement. This is due to the length of time the carcass is immersed in the chiller bath (typically between 1.5 and 3.0 hours). Assuming a disinfectant dosage that will result in 5.0 ppm "free residual," the resulting CT credit equates to 450–900 mg/L-min.

As can be seen from FIGS. 6 and 6B, the apparatus for employing the embodiments of the enhanced disinfection of carcasses in poultry chiller tanks 130 includes the following primary components: the disinfectant distribution system 132, pH control system 134 including acid control 140, on-line monitoring 136, organic mass removal system 138 (filtration for chiller tanks), a water reuse system 128, and/or an ozonating or chlorinating system 129.

The disinfectant distribution system 132 is designed to introduce, through direct injection into the process stream, the desired disinfectant. This sub-component may be advantageously configured for liquid/liquid injection and mixing, gas/liquid injection and/or solid dissolution followed by liquid/liquid injection. There are several common forms of disinfectant currently employed by the processing industry, including sodium hypochlorite, calcium hypochlorite, chlorine dioxide, ozone and others. It will be readily appreciated by those skilled in the art that each of these disinfectants will require a slightly different means of introduction into the process water stream.

The pH control system 134 is dependent upon the level of pH and the disinfectant employed. For sodium hypochlorite and calcium hypochlorite, the pH control system will preferably involve the introduction of acidification compound at a controlled and monitored rate. The rate of introduction (whether liquid/liquid or gas/liquid) will be monitored and proportionally controlled by the use of a PID or PLC type device to ensure that the pH level is controlled within a tight control band (i.e., for chlorine compounds 6.5–7.0 pH). On line monitoring allows for continuous monitoring of the treatment water by the use of pH probes 136 installed in the piping and distribution system. This assures that the pH level is at the desired "optimum" for the disinfectant employed.

An organic mass removal system 138 (filtration for chiller tanks) incorporates one or more steps designed to remove by physical separation, the organic contamination being constantly introduced to the carcass chiller tank(s) 130. Each animal carcass will have some materials that have not been removed in prior washing. These materials include soluble and insoluble fats, oils, skin, blood products and other contaminants as previously described. The filtration system 138 is designed to remove either all or a major portion of these "filterable solids" in order to reduce the oxidant demand in the chiller tank 130 and thus permit reaching a higher disinfection standard.

As an essential step in the poultry processing system, the chilling process includes vessels into which the poultry carcasses are introduced from the plant's processing lines to reduce temperature of the meat, control bacterial growth through chemical disinfection and hydrate the carcass within the USDA limits of acceptable water content. The process described herein is directed at maintaining the best conditions for chemical disinfection in poultry chiller tanks. As background for such processes, the U.S. poultry industry employs immersion chilling for poultry carcasses through the use of large volume, stainless steel tanks where the product is mechanically introduced from the processing line(s) after evisceration and inspection.

With reference to FIGS. 6B and 7, such poultry chillers 130 are connected to refrigeration loops, referred to in the industry as a "red water chiller(s)," for the purpose of rejecting heat from chilled water systems. Typically, these red water chiller recirculating systems 142 are closed loop heat exchangers operating with ammonia gas as the refrigerant and electric drive motors to provide the compression/expansion or state change of the refrigerant. The refrigeration chiller 142 typically operates as a closed recirculating loop, where the chiller acts as the heat exchanger to remove heat from the system water in order to maintain the USDA mandated temperature in the chiller tanks.

A mass removal system 138 is designed to continuously remove organic and solids content from the plant's chiller tanks 130 using screening, floatation, filtration and oxidation. The carcasses entering the chiller tanks 130 bring "contaminants" which may be of an organic or -inorganic nature and consist of fats, oils, grease, blood products, proteins, lipids and pieces of skin and organs that may have remained after the evisceration. Other inorganic contaminants typically consist of minerals dissolved into the water such as phosphates, nitrogen compounds and other constituents originating in the animal feed or the water used in washing and chilling. The chiller tanks 130 are filled before the first processing shift and are constantly refreshed with potable water during the plant's processing hours (the USDA maintains a requirement of one-half (½) gallon of makeup water per bird). The entering makeup water replaces a similar volume of chiller tank overflow being dispensed from the tank 130. This enables a refreshing of the chiller tank 130 to counteract the cumulative effects of concentration of the contamination brought into the tanks 130 with the carcasses.

It is known that the cumulative effects of constant introduction of the contaminants does negatively impact the effectiveness of carcass disinfection and microbial control. When analyzed for contaminant content, the water from chiller tanks 130 shows that there is a significant level of organic compounds that compete chemically with the microbial content for oxidizer demand. As such, most processing plants have had difficulties in controlling chlorine levels due to the presence of high organic loading.

The carcasses will typically remain in the chiller tanks 130 for between 145 minutes and several hours. The dwell time will be determined by the carcass weight, number of carcasses and efficiency of the chiller system in terms of refrigeration capacity. The controlling factor is the time required to achieve the temperature set by the USDA. The relatively long dwell times should provide an excellent opportunity for microbial control based on the previously described principals of contact time (CT). The limiting factor, however, is overcoming the organic loading resulting from the constant contaminant influx.

As discussed earlier, the process developed according to the present disclosure is directed at providing a continuous, on-line contaminant removal mechanism. The process is effected by the installation of mechanical separation, floatation and filtration devices 138 which are designed to remove organic compounds from the chiller tanks 130. This mass removal of the organic compounds is accompanied by the implementation of enhanced disinfection/microbial control using the most favorable chemistry for chlorination 132, 134, 140. The chemistry, as previously described herein, consists of the combination of pH control 134 and chlorine or other disinfectant injection 132.

The continuous separation, floatation, filtration mechanism 138 for mass removal of the contaminants being introduced into the chilled water tanks 130 is connected to the chiller tank 130 by way of interconnecting piping where a constant volume of water is pumped from the chiller tanks 130, sent to the contaminant removal apparatus, cleansed and returned to the chiller tanks 130. The process is designed to operate continuously. Maintenance of chiller tank water quality is dictated by the disinfection efficiency as measured by the chlorine monitoring devices.

With particular reference to FIG. 7, the chiller tank treatment system process is designed to allow for maximum flexibility of operations based upon the site-specific conditions, load profile and economics. The observed range of chiller system water quality varies significantly across the spectrum of poultry processing plants. In some cases, the operation of the chiller system, together with the size, weight and process rate of birds, will allow a solution that may not require the same mass removal of contaminants as others. A time weighted load factor should be analyzed to assist with the sizing and specification of the components and overall system configuration. This procedure can be accomplished by taking numerous samples of the bulk water in the chiller tanks 130 over a specified period of time. A plot of the contaminant loading will yield a load per hour rate or a load per carcass rate that is important to the sizing and configuration of the treatment solution. A target water quality is established based on the disinfection chemistry and a treatment system is sized to remove the required mass load of contaminants to consistently maintain the target water quality.

The first stage of the system involves pumping water from the chiller tanks 130, by way of a dedicated pump 170 to the treatment system's first stage unit operations. This stage includes a mechanical screening device 172 such as a double drum rotating type, where the influent water is introduced into the internal portion of the device. The double drum screen includes a larger mesh screen as its internal first stage, and a smaller mesh as its external second stage. As the solids are captured on either the internal or external screen surfaces, a traveling, high-pressure water spray nozzle, directed at the surface of the screen, forcibly removes the trapped solids and enhance the screen's ability to maintain flow capacities. The screened water is captured by gravity in a sump located below the screens. The sump is fitted with level sensors to interface with a pump fitted to the sump to allow for automatic operation and to prevent the pump from "dry cycling" when no water is available to pump.

The screened water, now having the preponderance of large solids removed, is pumped to the system's floatation unit 174. This floatation unit 174 could be either of the induced or dissolved air type. Selection of the best method is based on site-specific load characteristics and the targeted mass removal efficiency. Air floatation is well-documented in the literature and operates on well-understood principles of vertical bubble velocity and the ability to attract solids and colloidal materials. Simple skimming and/or overflow removes the floated material. Typical floatation devices are easily adaptable to accept chemical assistance in the form of coagulants, flocculants and other treatment chemicals designed to enhance removal efficiencies. The use of any such chemical assistance would be subject to FDA and USDA regulations and guidelines relating to food quality and safety. The now screened and floatation treated water is then flowed to the filtration device 176 which removes smaller solids. The selection of the filtration device 176, such as a media filter, will depend upon site-specific conditions. The media filter can use diatomaceous earth as its media and the filter vessel could be of a vacuum leaf, rotating vacuum drum, or pressure leaf design. The smaller solids not removed by the previous stages (screening and floatation) are trapped on the media filter's media matrix which, in the case of diatomaceous earth, has removal efficiencies capable of treating to small micron size particles. The effluent quality from such devices is quite high and is typically below 5 NTU's in turbidity. The treated water is now ready to be transferred back to the chiller tanks 130. At any point along the above identified filtration steps 138, the treated water can be monitored for turbidity via a monitoring device which allows the operator to monitor the system performance. Such a monitoring device can be installed anywhere in-line with alarms, feedback loops or recording devices, which enables total system performance and provides a base for implementing modifications.

Another example of the food safety benefits have been observed for a water reuse system, which utilizes the inventive features of this disclosure discussed above. In particular, an on-line reprocessing system, in accordance with the present disclosure, employs a pH controlled, chlorinated water regimen in the scalder, picker and multiple wash/rinse cabinets. The on-line reprocessing system applies a controlled concentration of a properly buffered chlorine solution for a sufficient period of time at key intervention points throughout the main processing line. Thus, on-line reprocessed carcasses are statistically indistinguishable from those reprocessed off-line. Additionally, overall food safety is improved through the increased pathogen reduction levels attained by exposing all carcasses to the on-line reprocessing system according to the present disclosure.

The on-line reprocessing system applies to poultry processing and uses Giardia (EPA set standard) as the reference pathogen. Giardia is employed because the contact time required for a given concentration of chlorine to inactivate Giardia is at least an order of magnitude more than that required to inactivate most viruses and bacteria. The contact time required to inactivate Giardia using chlorine can be mathematically approximated. This predictive formula was used to generate tables that show contact times required under different operating conditions to achieve targeted inactivation levels.

For example, a 6 log reduction in pathogens can be expected if 5½ minutes of contact with a 50 ppm residual chlorine solution buffered to pH 6.5 at 55° F. can be attained. Chlorine is the primary disinfectant used in the United States. It will inactivate cysts, ocysts, viruses and bacteria when given sufficient time to react with the microorganisms. Its effectiveness can be altered by changing certain variables associated with its application. In the on-line reprocessing system, chlorine concentrations and pH levels are controlled to maximize the formation of hypochlorous acid, which optimizes the chlorine's antimicrobial effect.

The on-line reprocessing system uses multiple intervention points in the processing plant to apply the controlled antimicrobial solution to the carcasses. This multi-step approach is designed to maximize the amount of time that the solution stays in contact with the poultry. It is recognized that the concentration of chlorine residual varies from maximum during the direct application points to minimum just before the following intervention point. The effect on reducing pathogens, however, is cumulative, so even though the chlorine concentration varies, the contact times of an average concentration can be estimated and summed. The total reduction in pathogens can then be predicted using the same algorithms that are used to determine treatment requirements to disinfect drinking water.

The contact time required to inactivate Giardia using chlorine is approximated by the following formula.

$$t = (0.2828 \times pH^{2.69} \times C^{0.15} \times 0.933^{(T-5)} \times L)/C$$

Where:
t=Contact time
pH=pH of water
C=Concentration of Free Chlorine residual (ppm)
T=Temperature (° C.)
L=Log removal Implementation of the on-line reprocessing system includes the following intervention points, water sources, chlorine concentrations and pH levels. In this particular process 5.7 minutes of potential pre-chiller contact time have been identified.

| Intervention Point | Contact time | Water Source* |
|---|---|---|
| Scalder** | 2 min., 1 second | Reuse Water |
| Picker | 1 min., 39 seconds | Reuse Water |
| Washer | 2 seconds | City Water |
| Pre-evisceration intervention time: | 3 min., 42 seconds | |
| 1st Outside Bird Wash | 3 seconds | City Water |
| 1st Inside/Outside Bird Wash | 5 seconds | City Water |

-continued

| | | |
|---|---|---|
| 2nd Inside/Outside Bird Wash | 9 seconds | City Water |
| 2nd Outside Bird Wash | 6 seconds | City Water |
| 3rd Outside Bird Wash | 4 seconds | City Water |
| Final Wash | 4 seconds | City Water |
| Post-evisceration intervention time: | 31 seconds | |
| Time between Intervention Points (see assumptions below) | 1 min., 30 seconds | |
| Total Contact Time | 5 min., 43 seconds (or 5.7 minutes) | |

Assumptions regarding contact time between intervention points:
1. Chlorine concentration will decrease to zero after 20 seconds;
2. Carcass will stay wet for 20 seconds after a direct treatment;
3. Therefore, the equivalent of an additional 10 seconds of contact time at the original treatment concentration will be received for each intervention point; and
4. Nine (9) pre-chiller intervention points x 10 sec = 1 minute, 30 seconds.

*Water Source: Reuse water from the water reuse system will be used in the scalder and picker. This water includes specific surfactant like molecules resulting from saponified fatty acids in the reconditioned process water. This reuse water decreases the water's surface tension resulting in a "wetter" bird, which facilitates the removal of fecal coliform and other microorganisms from the skin of the carcass. The water source for other intervention points will be city water. All treatment water used in the on-line reprocessing system will be maintaained at 50 PPM chlorine and at a pH of 6.5.
**Scalder: Due to the heavy organic load, it would be difficult to achieve a free chlorine residual in the scalder. The addition of chlorine induces an anti-microbial benefit by causing the production of chloramines. Chloramine disinfection is widely used in municipal distribution systems. Treatment in the scalder is accomplished by controlling chlorine and pH levels in the make-up water rather than in the scalder itself.

By applying a specified concentration of a pH controlled chlorinated solution for a given amount of time, the on-line reprocessing system will provide a level of pathogen reduction that will provide the poultry processor with significant food safety benefits.

The following tables display the contact times required to achieve the indicated levels of pathogen reduction for various combinations of temperature, pH and chlorine concentration. Only contact times that are less than or equal to the 5.7 minute contact time example are displayed so that the range of required operating parameters can be seen at a glance. The contact times in these tables are derived from the formula discussed above.

Contact Times (Minutes) for 99.9% (3 log) Inactivation

| | | | | | | |
|---|---|---|---|---|---|---|
| Log Removal Required | | 3 | | | | |
| Max Contact Time | | 5.7 | | | | |
| Temperature (Degrees F.) | | 40 | | | | |

| Residual | pH | | | | | |
|---|---|---|---|---|---|---|
| (ppm) | 6.0 | 6.5 | 7.0 | 7.5 | 8.0 | 8.5 |
| 5 | — | — | — | — | — | — |
| 10 | — | — | — | — | — | — |
| 15 | — | — | — | — | — | — |
| 20 | — | — | — | — | — | — |
| 25 | — | — | — | — | — | — |
| 30 | — | — | — | — | — | — |
| 35 | 5.3 | — | — | — | — | — |
| 40 | 4.8 | — | — | — | — | — |
| 45 | 4.3 | 5.3 | — | — | — | — |
| 50 | 3.9 | 4.9 | — | — | — | — |

Contact Times (Minutes) for 99.99% (4 log) Inactivation

| Log Removal Required | 3 |
| Max Contact Time | 5.7 |
| Temperature (Degrees F.) | 55 |

| Residual (ppm) | pH 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | 4.8 | — | — | — | — | — |
| 25 | 4.0 | 4.9 | — | — | — | — |
| 30 | 3.4 | 4.2 | 5.2 | — | — | — |
| 35 | 3.0 | 3.7 | 4.5 | 5.4 | — | — |
| 40 | 2.7 | 3.3 | 4.0 | 4.9 | — | — |
| 45 | 2.4 | 3.0 | 3.7 | 4.4 | 5.2 | — |
| 50 | 2.2 | 2.7 | 3.3 | 4.0 | 4.8 | 5.6 |

| Log Removal Required | 4 |
| Temperature (Degrees F.) | 40 |
| Max Contact Time | 5.7 |

| Residual (ppm) | pH 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | — | — | — | — | — | — |
| 25 | — | — | — | — | — | — |
| 30 | — | — | — | — | — | — |
| 35 | — | — | — | — | — | — |
| 40 | — | — | — | — | — | — |
| 45 | — | — | — | — | — | — |
| 50 | 5.2 | — | — | — | — | — |

| Log Removal Required | 3 |
| Max Contact Time | 5.7 |
| Temperature (Degrees F.) | 70 |

| Residual (ppm) | pH 6.0 | 6.5 | 7.0 | 7.5 | 8.0 | 8.5 |
|---|---|---|---|---|---|---|
| 5 | — | — | — | — | — | — |
| 10 | 4.9 | — | — | — | — | — |
| 15 | 3.4 | 4.3 | 5.2 | — | — | — |
| 20 | 2.7 | 3.3 | 4.1 | 4.9 | — | — |
| 25 | 2.2 | 2.8 | 3.4 | 4.1 | 4.8 | 5.7 |
| 30 | 1.9 | 2.4 | 2.9 | 3.5 | 4.1 | 4.9 |
| 35 | 1.7 | 2.1 | 2.5 | 3.1 | 3.6 | 4.3 |
| 40 | 1.5 | 1.9 | 2.3 | 2.7 | 3.2 | 3.8 |
| 45 | 1.4 | 1.7 | 2.0 | 2.5 | 2.9 | 3.5 |
| 50 | 1.2 | 1.5 | 1.9 | 2.3 | 2.7 | 3.2 |

| Log Removal Required | 4 |
| Temperature (Degrees F.) | 55 |
| Max Contact Time | 5.7 |

| Residual (ppm) | pH 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | — | — | — | — | — | — |
| 25 | 5.3 | — | — | — | — | — |
| 30 | 4.5 | 5.6 | — | — | — | — |
| 35 | 4.0 | 4.9 | — | — | — | — |
| 40 | 3.6 | 4.4 | 5.4 | — | — | — |
| 45 | 3.2 | 4.0 | 4.9 | — | — | — |
| 50 | 2.9 | 3.6 | 4.5 | 5.4 | — | — |

| Log Removal Required | 3 |
| Temperature (Degrees F.) | 85 |
| Max Contact Time | 5.7 |

| Residual (ppm) | pH 6.0 | 6.5 | 7.0 | 7.5 | 8.0 | 8.5 |
|---|---|---|---|---|---|---|
| 5 | 4.9 | — | — | — | — | — |
| 10 | 2.7 | 3.4 | 4.1 | 5.0 | — | — |
| 15 | 1.9 | 2.4 | 2.9 | 3.5 | 4.2 | 4.9 |
| 20 | 1.5 | 1.9 | 2.3 | 2.8 | 3.3 | 3.9 |
| 25 | 1.3 | 1.6 | 1.9 | 2.3 | 2.7 | 3.2 |
| 30 | 1.1 | 1.3 | 1.6 | 2.0 | 2.3 | 2.7 |
| 35 | 0.9 | 1.2 | 1.4 | 1.7 | 2.0 | 2.4 |
| 40 | 0.8 | 1.0 | 1.3 | 1.5 | 1.8 | 2.1 |
| 45 | 0.8 | 0.9 | 1.1 | 1.4 | 1.6 | 1.9 |
| 50 | 0.7 | 0.9 | 1.1 | 1.3 | 1.5 | 1.8 |

| Log Removal Required | 4 |
| Temperature (Degrees F.) | 70 |
| Max Contact Time | 5.7 |

| Residual (ppm) | pH 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | 4.6 | 5.7 | — | — | — | — |
| 20 | 3.6 | 4.5 | 5.4 | — | — | — |
| 25 | 3.0 | 3.7 | 4.5 | 5.4 | — | — |
| 30 | 2.5 | 3.2 | 3.9 | 4.6 | 5.5 | — |
| 35 | 2.2 | 2.8 | 3.4 | 4.1 | 4.8 | — |
| 40 | 2.0 | 2.5 | 3.0 | 3.6 | 4.3 | 5.1 |
| 45 | 1.8 | 2.2 | 2.7 | 3.3 | 3.9 | 4.6 |
| 50 | 1.6 | 2.0 | 2.5 | 3.0 | 3.6 | 4.2 |

| Log Removal Required | | | 4 | | |
|---|---|---|---|---|---|
| Temperature (Degrees F.) | | | 85 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | 3.6 | 4.5 | 5.5 | — | — | — |
| 15 | 2.6 | 3.2 | 3.9 | 4.7 | 5.6 | — |
| 20 | 2.0 | 2.5 | 3.1 | 3.7 | 4.4 | 5.1 |
| 25 | 1.7 | 2.1 | 2.5 | 3.0 | 3.6 | 4.3 |
| 30 | 1.4 | 1.8 | 2.2 | 2.6 | 3.1 | 3.6 |
| 35 | 1.3 | 1.6 | 1.9 | 2.3 | 2.7 | 3.2 |
| 40 | 1.1 | 1.4 | 1.7 | 2.0 | 2.4 | 2.9 |
| 45 | 1.0 | 1.3 | 1.5 | 1.8 | 2.2 | 2.6 |
| 50 | 0.9 | 1.1 | 1.4 | 1.7 | 2.0 | 2.4 |

Contact Times (Minutes) for 99.999% (5 log) Inactivation

| Log Removal Required | | | 5 | | |
|---|---|---|---|---|---|
| Temperature (Degrees F.) | | | 40 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | — | — | — | — | — | — |
| 25 | — | — | — | — | — | — |
| 30 | — | — | — | — | — | — |
| 35 | — | — | — | — | — | — |
| 40 | — | — | — | — | — | — |
| 45 | — | — | — | — | — | — |
| 50 | — | — | — | — | — | — |

| Log Removal Required | | | 5 | | |
|---|---|---|---|---|---|
| Temperature (Degrees F.) | | | 55 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | — | — | — | — | — | — |
| 25 | — | — | — | — | — | — |
| 30 | 5.7 | — | — | — | — | — |
| 35 | 5.0 | — | — | — | — | — |
| 40 | 4.4 | 5.5 | — | — | — | — |
| 45 | 4.0 | 5.0 | — | — | — | — |
| 50 | 3.7 | 4.6 | 5.6 | — | — | — |

| Log Removal Required | | | 5 | | |
|---|---|---|---|---|---|
| Temperature (Degrees F.) | | | 70 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | 4.5 | 5.6 | — | — | — | — |
| 25 | 3.7 | 4.6 | 5.6 | — | — | — |
| 30 | 3.2 | 3.9 | 4.8 | — | — | — |
| 35 | 2.8 | 3.5 | 4.2 | 5.1 | — | — |
| 40 | 2.5 | 3.1 | 3.8 | 4.5 | 5.4 | — |
| 45 | 2.3 | 2.8 | 3.4 | 4.1 | 4.9 | — |
| 50 | 2.1 | 2.6 | 3.1 | 3.8 | 4.5 | 5.3 |

| Log Removal Required | | | 5 | | |
|---|---|---|---|---|---|
| Temperature (Degrees F.) | | | 85 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | 4.5 | 5.6 | — | — | — | — |
| 15 | 3.2 | 4.0 | 4.9 | — | — | — |
| 20 | 2.5 | 3.1 | 3.8 | 4.6 | 5.5 | — |
| 25 | 2.1 | 2.6 | 3.2 | 3.8 | 4.5 | 5.3 |
| 30 | 1.8 | 2.2 | 2.7 | 3.3 | 3.9 | 4.6 |
| 35 | 1.6 | 1.9 | 2.4 | 2.9 | 3.4 | 4.0 |
| 40 | 1.4 | 1.7 | 2.1 | 2.5 | 3.0 | 2.6 |
| 45 | 1.3 | 1.6 | 1.9 | 2.3 | 2.7 | 3.2 |
| 50 | 1.2 | 1.4 | 1.8 | 2.1 | 2.5 | 3.0 |

Contact Times (Minutes) for 99.9999% (6 log) Inactivation

| Log Removal Required | | | 6 | | |
|---|---|---|---|---|---|
| Temperature (Degrees F.) | | | 40 | | |
| Max Contact Time | | | 5.7 | | |
| Residual | pH | | | | |
| (ppm) | 6.0 | 6.5 | 7.0 | 7.5 | 8.0 | 8.5 |
|---|---|---|---|---|---|---|
| 5 | — | — | — | — | — | — |
| 10 | — | — | — | — | — | — |
| 15 | — | — | — | — | — | — |
| 20 | — | — | — | — | — | — |
| 25 | — | — | — | — | — | — |
| 30 | — | — | — | — | — | — |
| 35 | — | — | — | — | — | — |
| 40 | — | — | — | — | — | — |
| 45 | — | — | — | — | — | — |
| 50 | — | — | — | — | — | — |

| Log Removal Required | | | 6 | | |
|---|---|---|---|---|---|
| Temperature (Degrees F.) | | | 55 | | |
| Max Contact Time | | | 5.7 | | |
| Residual | pH | | | | |
| (ppm) | 6.0 | 6.5 | 7.0 | 7.5 | 8.0 | 8.5 |
| 5 | — | — | — | — | — | — |
| 15 | — | — | — | — | — | — |
| 20 | — | — | — | — | — | — |
| 25 | — | — | — | — | — | — |
| 30 | — | — | — | — | — | — |
| 35 | — | — | — | — | — | — |
| 40 | 5.3 | — | — | — | — | — |
| 45 | 4.8 | — | — | — | — | — |
| 50 | 4.4 | 5.5 | — | — | — | — |

| Log Removal Required | | | 6 | | |
|---|---|---|---|---|---|
| Temperature (Degrees F.) | | | 70 | | |
| Max Contact Time | | | 5.7 | | |
| Residual | pH | | | | |
| (ppm) | 6.0 | 6.5 | 7.0 | 7.5 | 8.0 | 8.5 |
| 5 | — | — | — | — | — | — |
| 10 | — | — | — | — | — | — |
| 15 | — | — | — | — | — | — |
| 20 | 5.4 | — | — | — | — | — |
| 25 | 4.5 | 5.5 | — | — | — | — |
| 30 | 3.8 | 4.7 | — | — | — | — |
| 35 | 3.4 | 4.2 | 5.1 | — | — | — |
| 40 | 3.0 | 3.7 | 4.5 | 5.5 | — | — |
| 45 | 2.7 | 3.4 | 4.1 | 4.9 | — | — |
| 50 | 2.5 | 3.1 | 3.7 | 4.5 | 5.4 | — |

| Log Removal Required | | | 6 | | |
|---|---|---|---|---|---|
| Temperature (Degrees F.) | | | 85 | | |
| Max Contact Time | | | 5.7 | | |
| Residual | pH | | | | |
| (ppm) | 6.0 | 6.5 | 7.0 | 7.5 | 8.0 | 8.5 |
| 5 | — | — | — | — | — | — |
| 10 | 5.5 | — | — | — | — | — |
| 15 | 3.9 | 4.8 | — | — | — | — |
| 20 | 3.0 | 3.8 | 4.6 | 5.5 | — | — |
| 25 | 2.5 | 3.1 | 3.8 | 4.6 | 5.4 | — |
| 30 | 2.1 | 2.7 | 3.2 | 3.9 | 4.6 | 5.5 |
| 35 | 1.9 | 2.3 | 2.8 | 3.4 | 4.1 | 4.8 |
| 40 | 1.7 | 2.1 | 2.5 | 3.1 | 3.6 | 4.3 |
| 45 | 1.5 | 1.9 | 2.3 | 2.8 | 3.3 | 3.9 |
| 50 | 1.4 | 1.7 | 2.1 | 2.5 | 3.0 | 3.5 |

A number of experiments have been performed in order to evaluate specific intervention points in the on-line reprocessing system. All on-line experiments referenced below were conducted on carcasses that had failed inspection for visual fecal contamination. The experiments included the following:

The on-line reprocessing system concept was validated by a series of laboratory experiments performed to illustrate the effect on microorganism populations after short duration exposure to a pH-controlled solution of chlorinated water.

A multiple treatment point disinfection process combined with serial carcass washing reduces pathogen levels sufficiently to justify on-line reprocessing. The specific objectives of the on-line reprocessing system are two fold: 1) to remove visible fecal material or other contaminants from the carcasses resulting from the mechanical evisceration process; and 2) to introduce an enhanced antimicrobial treatment agent at multiple stages to improve food safety by reducing total microbial levels.

Physical removal of the visible fecal material and other contaminants may be carried out by serial carcass washing stages (inside/outside carcass washing cabinets and outside carcass washing cabinets) where medium pressure, high volume water spraying is best employed. Application of a USDA approved chlorinating agent at a controlled pH for optimum disinfection, at multiple conditioning stages (scalder, picker, post pick spray wash, inside/outside carcass wash and outside carcass wash) with the best practical control methods significantly reduces microbial levels on all carcasses during processing.

The process described herein is designed to employ the advantages of controlled chlorination at optimum pH levels together with the proven effectiveness of increased contact time through the implementation of multiple stage treatments of the carcass during slaughter, evisceration, washing and chilling.

During poultry processing operations the reduction of microorganisms must be accomplished in a limited amount of time, with a limited amount of water. To optimize disinfection and water consumption, the majority of the added chlorine should be in the form of hypochlorous acid. The following experiments conducted at a poultry processing plant demonstrate the effectiveness of this technique in a laboratory simulation.

Processing Line Simulation

Sample Selection

Each of six experiments performed at the test plant required nine partially processed carcasses. Half of the experiments used carcasses taken after the final inspection and half of the experiments used carcasses taken after the final wash.

As shown in Table 8 reproduced below, of the nine carcass samples used in each experiment, three carcasses were not treated and used to establish a baseline. Three carcasses were treated with the on-line reprocessing system (i.e., chlorine plus pH control) according to the present disclosure. Such on-line reprocessing system may also be referenced herein as the PathX™ system. The remaining three carcass samples were treated in a control aqueous solution, with a chlorine concentration equal to the on-line reprocessing system but without pH control.

TABLE 8

Sample Selection

| Category | Total |
|---|---|
| Untreated Carcasses | 3 |
| PathX ™ Treated Carcasses | 3 |
| Control Treated Carcasses | 3 |
| Total Carcasses per Experiment | 9 |

Experimental Parameters

Experimental parameters in the processing line simulation experiments included:

1.) pH—different for the control group and on-line reprocessing system; 2.) contact time—equal for the control group and on-line reprocessing system; and 3.) chlorine concentration—equal for the control group and on-line reprocessing system for each of the six experiments. The concentrations between experiments ranged from 10–40 ppm.

Processing Solution Preparation

The six experiments were performed with the following steps. Six, 3.5-gallon buckets were cleaned and air stones were installed to provide agitation. The buckets were filled with three gallons of delivered municipal water. The water in the controlled buckets had the pH adjusted to the previous 75-day average of delivered municipal water. This average was pH 8.05. The appropriate amount of sodium hypochlorite was then added. The water in the on-line reprocessing buckets had the appropriate amount of chlorine added and then the pH was adjusted to the appropriate pH. This simulation was designed to evaluate the impact of the on-line reprocessing system within the constraints of the short contact times found in a processing line. The carcasses were immersed in the buckets for one minute.

Carcass Sample Selection

To avoid sampling prejudices, a "count five and take the fifth" selection technique was used. Each sample was removed from the processing line using an inverted sterilized bag. The bagged carcasses were put into a cart with ice and brought to the on-line reprocessing system area and immediately tested.

Processing Line Simulation

At the on-line reprocessing system area, the carcasses were taken from the individual sterile bags and put into individual buckets. Individual buckets were used to prevent cross contamination. With all the carcasses in the buckets, the mixing system and timer were started.

After one minute the reactions were stopped by removing the chlorine from the system with the addition of sodium thio sulfate. The carcasses were removed from the buckets and placed in individual sterile bags. The three untreated carcasses were tested as well as three of the on-line reprocessing system and three of the control carcasses. The test samples were sent for analysis.

Analytical Testing

The test samples were analyzed for Total Aerobic Plate counts, *E. coli* and Total Coliform. The tests were performed by laboratory personnel who had been trained in USDA approved procedures. These analyses were reported in colony forming units (CFU's).

*E. coli* and Total Coliform

Step 1 Sampling: The test samples were prepared using a "Whole Bird Carcass Rinse" method. In this method, 400 milliliters of refrigerated Butterfield's solution is poured over a carcass, while in a sterile bag. The bag is closed and the sample carcass is rinsed for 1 minute by shaking the carcass in a 1-foot arc. Each original test sample was poured back into the original Butterfield's jar from the sterile bag.

Step 2 Plating: A 1.0-milliliter sample was plated directly on *E. coli* Petrifilm. The first dilution was 10 milliliters of test sample into 90 milliliters of sterile buffered peptone solution. Additional dilutions used 1 milliliter of the previous dilution added to 9 milliliters of sterile buffered peptone solution.

Step 3 Incubation: The Petrifilms were incubated for 48+/−2 hours at a temperature of 35+/−0.5° C.

Step 4 Identification: *E. Coli* colonies were identified as blue colonies surrounded by gas. Total Coliform colonies were identified as the *E. coli*, blue colonies surrounded by gas, and the red colonies surrounded by gas.

Aerobic Plate Counts (APC)

Step 1 Sampling: The test samples were prepared using the "Whole Bird Carcass Rinse" as described above.

Step 2 Plating: A 1.0-milliliter sample was plated directly on APC Petrifilm. The first dilution was 10 milliliters of test sample into 90 milliliters of sterile buffered peptone solution. Additional dilutions used 1 milliliter of the previous dilution added to 9 milliliters of sterile buffered peptone solution.

Step 3 Incubation: The APC Petrifilms were incubated for 48+/−2 hours at a temperature of 35+/−0.50 C.

Step 4 Identification: Any colonies that grew on the APC Petrifilms were counted as Aerobic Plate Counts.

Figure 8:
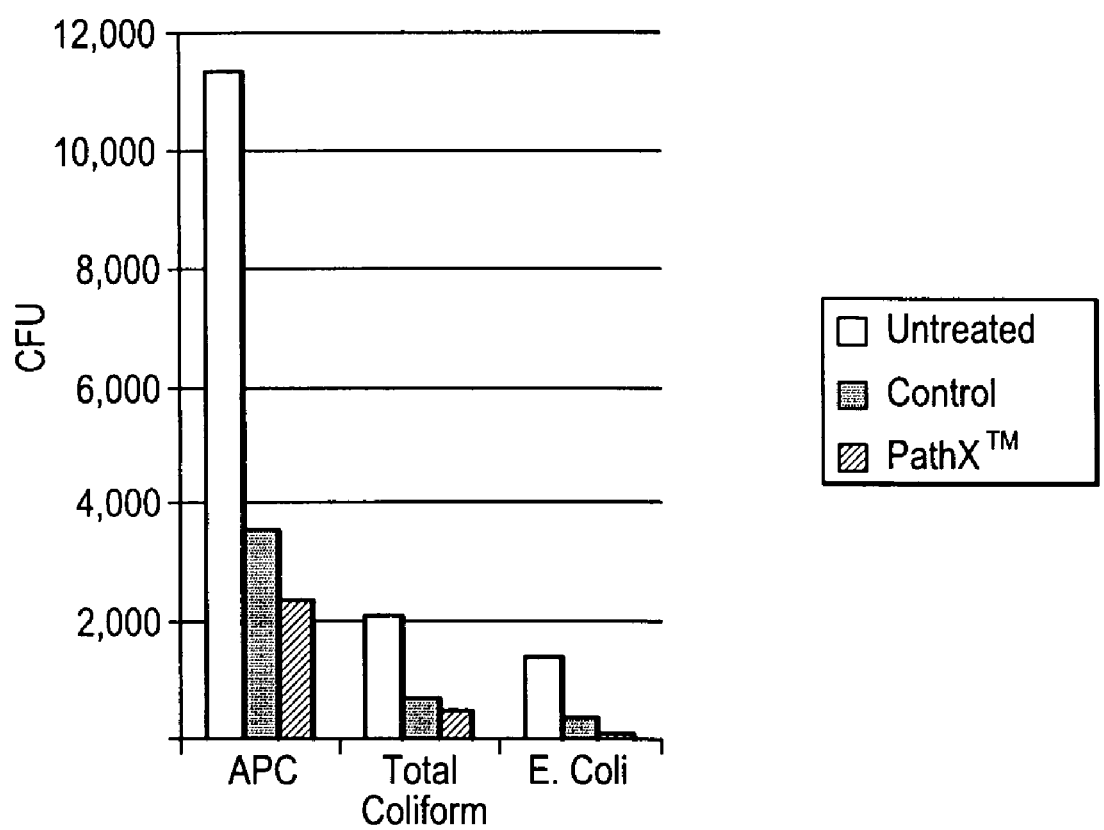
FIG. 8 illustrates results of testing of the on-line reprocessing system for *E. coli*, total coliform and aerobic plate counts (APC) according to the present disclosure.

Fifty-four carcasses were tested during the one-minute contact time experiments. This simulation was meant to replicate the short contact times in the processing line. The one-minute contact data is therefore relevant to the evaluation of the on-line reprocessing system. This data is shown in Table 9 and FIG. 8.

TABLE 9

| | 1 Minute Treatment | | |
|---|---|---|---|
| | APC (CFU) | Total Coliform (CFU) | *E.coli* (CFU) |
| Untreated | 11,402 | 2,096 | 1,424 |
| Control | 3,540 | 722 | 406 |
| On-line reprocessing system (PathX ™) | 2,382 | 518 | 123 |

The disclosed laboratory simulation of one step in a poultry processing line dictates that 1.) antimicrobial treatment beneficially reduces total microbial counts on poultry carcasses, and 2.) providing process control to the antimicrobial treatment of an on-line reprocessing system produces substantially lower bacteria counts than the untreated process control. Current chlorine chemistry theory supports these results. At a neutral pH, the majority of available chlorine is in the form of hypochlorous acid. The hypochlorous acid reacts more quickly than hypochlorite to reduce microorganisms.

These experiments did not have a continuous re-supply of chlorine and still showed substantially improved reduction of microorganisms. The experiments also did not evaluate the effects of continuous exposure or cumulative effects of multiple-point treatment. The on-line reprocessing system of the present disclosure is designed to utilize multiple point treatments in its actual operation and may incorporate varying supplies, including a continuous re-supply of chlorine.

In a scalder experiment, the potential impact on overall pathogen reduction of treating scalder makeup water was determined. Results show that carcasses scalded when makeup water was comprised of reuse water, as previously described herein, with 20 ppm of buffered chlorine added, averaged over 50% lower *E. coli* levels than those scalded when using unbuffered chlorinated city makeup water. The carcasses were tested just prior to entering the chiller. In addition to the benefit provided by pH control, the other difference between the reuse water and city water is a small amount of dissolved fatty acids, which enter the reuse process water. These fatty acids are saponified yielding specific surfactant-like molecules in the reuse water. Adding a surfactant to water decreases the water's surface tension. With decreased surface tension, the reuse water is able to cover the surface of the carcass better resulting in a "wetter" bird, that is, the reuse water better penetrates the pores and skin membranes of the carcasses, which facilitates the removal of fecal coliform and other microorganisms from the skin.

The scalder experiments evaluated the benefit of scalding and picking carcasses with reuse water vs. city water. Only carcasses that had failed inspection for visual fecal contamination were used in these experiments. The on-line reprocessing system demonstrates the significance of using multiple intervention steps to reduce pathogens in poultry processing by increasing carcass contact time with an antimicrobial intervention regimen. These experiments examined microbial control when:

1. City water with 20 PPM of chlorine was used in the scalders ("city water"), and
2. Reuse water from the water reuse system with 20 PPM of chlorine and controlled pH was used in the scalders ("reuse water").

Carcasses, which had been placed on the reprocessing line for visual fecal contamination, were removed from the reprocessing line and reserved for on-line processing during regularly scheduled evisceration line breaks. During these breaks, the reserved carcasses were re-hung on the main processing line prior to any wash cabinets, run through the standard wash cabinets and removed after final rinse on the evisceration line. The carcasses were then bagged and rinsed to provide samples for *E. coli* enumeration and a *Salmonella* positive/negative test. The scalder was the only point where carcasses were exposed to reuse water. All wash cabinets utilized regular city water without any addition of chlorine or pH control.

In the scalders, carcasses are immersed in hot water to facilitate the removal of feathers. The hot water opens the pores in the carcass skin, which presents a major opportunity to reduce pathogens in otherwise difficult-to-treat areas. The communal bath, however, presents the potential for cross contamination. Hence, the scalder is a significant intervention point for both pathogen reduction on the carcasses and for mitigating cross-contamination.

A summary of the data from the experiments are disclosed in Tables 10 and 11, below:

TABLE 10

Summary of *E. coli* Data

|  | City Water Chlorinated No pH Control | Reuse Water Chlorinated With pH Control | Percent Reduction |
|---|---|---|---|
| Carcasses Sampled | 120 | 150 |  |
| Average *E. coli* (CFU)lml | 631 | 305 | 52% |
| Average *E. coli* CFU lml Minus 2 Max #s/day | 319 | 118 | 63% |

*E. coli* data show a 50% +reduction in *E. coli* levels when carcasses were scalded using reuse water versus carcasses that had been scalded using city water. All scalder makeup water, whether reuse water or city water, was chlorinated to 20 ppm.

To compensate for carcasses that would not remain on the main processing line due to excessive visible fecal material, the *E. coli* colony forming unit averages were recalculated after discarding the maximum 2 values of the 30 values calculated each day. These carcasses have excessive fecal contamination and would require additional manual reprocessing.

One of the major differences between carcasses treated in the scalder with city water vs. reuse water was the number of carcasses with *E. coli* counts of greater than 100 CFU. USDA *E. coli* standards for post-chiller inspection call for a moving window of 13 carcasses that are sampled. *E. coli* counts fall into three categories (0–100, 101–1000, 1001+). Within the 13-sample window, there can be 3 that are in the 101–1000 category as long as the other 10 are below 100. Any carcass over 1000 causes a failure. As shown below at Table 11, 24% of carcasses treated with reuse water in the scalder had *E. coli* counts of greater than 100 CFU while 36% of carcasses treated with city water had counts greater than 100 CFU. In addition, there was a substantial difference in the average counts of those samples between those treated with city water versus reuse water. For reuse water treated carcasses with counts greater than 100 CFU, the average count was 321 CFU. For city water treated carcasses that had counts greater than 100 CFU, the average was 808 CFU. Again, all of these counts were taken pre-chiller. Far fewer reuse water treated carcasses had *E. coli* counts greater than 100 CFU, and those that did had substantially lower counts than those treated with city water.

TABLE 11

*E. coli* Counts Greater Than 100 CFU

|  | Reuse Water | City Water |
|---|---|---|
| % of Carcasses with >100 CFU | 24% | 36% |
| Average Count | 321 CFU | 808 CFU |

In a rinse cabinets experiment, city water was used with 40–50 ppm chlorine and buffered pH in rinse cabinets on the reprocess line, whereby greater than 50% reductions in *Salmonella* positives and consistent reductions in *E. coli* levels were achieved. Consistent with the on-line reprocessing system, those carcasses that went through three rinse cabinets rather than two, experienced more contact time and therefore showed the greatest improvement.

On-line reprocessing experiments were performed for a period of five weeks. The conditions included:

Week 1—Start-up and initial balancing of system;

Week 2—Final balance and initial tests with non-on-line reprocessing system water with 2 spray cabinets;

Week 3—on-line reprocessing system experiments with 2 spray cabinets;

Week 4—on-line reprocessing system experiments with 3 spray cabinets; and

Week 5—on-line reprocessing system experiments with 3 spray cabinets.

The on-line reprocessing system equipment delivered a chlorine dose of 40 to 50 PPM to the spray cabinets, pH was controlled at levels between 6.0 and 7.0. Both the pH and chlorine dosages were closely monitored and tightly controlled. There were no problems with chlorine off gassing. Reduced pH water did not generate any obvious problems with corrosion.

Each week there were four (4) days of experimentation. Each day, forty (40) carcasses, which had failed for visual fecal contamination, were used for these experiments. Twenty (20) of those carcasses were tested for *Salmonella* and *E. coli* prior to going through the birdwasher process. An additional twenty (20) carcasses were tested after they went through the birdwasher process.

Table 12 contains a summary of *E. Coli* data and Table 13 contains a summary of *Salmonella* data.

TABLE 12

Summary of *E. Coli* Data

|  | Rinse Cabinets | pH | *E. coli* Post Inspection | *E. coli* Post PathX ™ | *E. coli* Post PathX ™ −2 max #'s |
|---|---|---|---|---|---|
| Week 2 | 2 | 7 | 1898 | | |
| Week 3 | 2 | 6.5 | 3775 | 574 | 163 |
| Week 4 | 3 | 6 | 1251 | 390 | 88 |
| Week 5 | 3 | 6 | 2614 | 123 | 62 |

*E. coli*

Table 12 shows there is a substantial reduction in *E. coli* after 2 rinses and a pH of 6.5 on the reprocessing line, and a greater reduction with 3 rinses and a pH of 6.0 on the reprocessing line.

To compensate for the carcasses that would not remain on the main processing line, due to excessive visible fecal material, the *E. coli* colony forming unit averages were recalculated after discarding the maximum 2 values of the 20 values calculated each day. This data represents the maximum of 10% (23 of 240 or 2 of 20) of the values calculated each day after inspection and after rinsing. This data reduction technique was used to allow for the carcasses that showed a substantial amount of visible fecal material, which was detected before and after the spray cabinets. These carcasses have excessive fecal contamination and would require additional manual reprocessing.

Recalculating the *E. coli* averages showed a further decrease in the average CFU's of *E. coli* on each carcass. The data without the maximum 2 values show that with controlled pH and 3 spray cabinets, *E. coli* can be held under the 100 CFU limit.

TABLE 13

Summary of Salmonella Data

|  | Rinse Cabinets | pH | Positive | Negative | Positive | Negative |
|---|---|---|---|---|---|---|
|  |  |  | Non-PathX ™ |  | Post Inspection |  |
| Week 2 | 2 | 7 | 21 | 59 | 31 | 49 |
|  |  |  | PathX ™ |  | Post Inspection |  |
| Week 3 | 2 | 6.5 | 3 | 57 | 13 | 47 |
| Week 4 | 3 | 6 | 8 | 72 | 16 | 64 |
| Week 5 | 3 | 6 | 21 | 59 | 48 | 32 |

*Salmonella*

Week 2: The non-on-line reprocessing system treatment reduced the number of *Salmonella* positives with 2 birdwashers from 31 of 80 to 21 of 80 carcasses (39% to 26%).

Week 3: The on-line reprocessing system process and 2 birdwashers reduced the number of *Salmonella* positives from 13 of 60 to 3 of 60 (21% to 5%) carcasses. The *Salmonella* data from one day in week 3 is not available.

Weeks 4 and 5: The on-line reprocessing system process and 3 birdwashers reduced the number of *Salmonella* positives from 64 of 160 to 29 of 160 carcasses (40% to 18%).

As shown in Table 13, over weeks 3, 4 and 5, during which time the fully operational on-line reprocessing system experiments were run, the *Salmonella* positive percentage dropped from 35% (77 of 220) post inspection to 14.5% (32 of 220) following on-line reprocessing system treatment in the bird washers.

Using the above criteria for *E. coli* and *Salmonella* analysis, it appears carcasses, which now would be placed on the reprocessing line, may be allowed to stay on the main processing line.

In a chiller experiment, a study was conducted to determine the effect on bacterial counts of using pH-controlled chlorination in the chiller. Although the focus of on-line reprocessing system development has been on antimicrobial intervention during pre-chiller processing, it is recognized that the amount of time the carcass spends in the chiller presents a substantial pathogen reduction opportunity to further enhance overall food safety.

Sample Collection and Transportation

Thirty whole ready-to-cook broiler chicken carcasses were obtained from the chiller exit of a commercial broiler processing facility in each of three trials for each test type (*E. coli* or *Salmonella*). The carcasses were individually bagged in sterile polyethylene bags and transported to the laboratory on ice (3000 cc $O_2$ at 22.8° C. per $m^2$ per 24 h at 1 atm). Carcasses were randomly separated into three groups containing ten carcasses in each group.

Sample Inoculation

Each of the thirty carcasses were inoculated with 1 milliliter each of twenty-four hour old actively growing cultures of generic Escherichia coli and naladixic acid resistant *Salmonella*. Carcasses were inoculated by placing 1 milliliter of each bacterial suspension onto the breast skin of the carcass and spreading with a sterile bent glass rod.

Attachment

Each carcass was allowed to remain at room temperature for 1 hour to allow bacterial attachment prior to treatment.

Treatment

Each of ten carcasses were placed into three 44-gallon containers with the following solutions:

1.) tap water (the tap water tank);

2.) tap water containing 50 ppm chlorine at a floating pH of approximately 9.0 (the control tank); and 3.) tap water containing 50 ppm chlorine at a pH of 6.5 (the on-line reprocessing system according to the present disclosure, the PathX™ tank).

The carcasses were allowed to remain in these solutions for 1 hour. In trial 1, the chlorine level was allowed to fluctuate during the treatment period. In trials 2 and 3, additional chlorine and buffer were added to maintain the set point pH and chlorine concentrations in the on-line reprocessing system tank. Chlorine was added to the control tank to maintain the chlorine concentration. After the one-hour time duration of the experiment, sodium thiosulfate was added to each tank to remove the free chlorine in the solution.

*E. coli* and *Salmonella*

Step 1 Sampling: The carcasses were removed from the treatment solution, placed into sterile bags, and rinsed using the whole carcass rinse procedure (as described above). Using this method, 100 milliliters of refrigerated sterile deionized water was poured over the carcasses in the sterile bag. The bag was closed and the carcass was rinsed using 50 vigorous shakes. The original test sample was collected from the sterile bag.

Step 2 Plating: 1.0-milliliter of the test sample was placed into a SimPlate® coliform and *E. coli* most-probable-number test kit to enumerate *E. coli*. For *Salmonella*, a 1.0-milliliter test sample was serially diluted and plated on brilliant green agar containing naladixic acid. Only the naladixic acid *Salmonella* were able to grow on this medium.

Step 3 Incubation: The SimPlate® kits were incubated at 35° C. for 48 hours and were counted using a black light to determine MUG positive wells (indicates the presence of *E. coli*). *Salmonella* plates were incubated at 35° C. for 48 hours and colonies were counted by hand.

Figure 9:
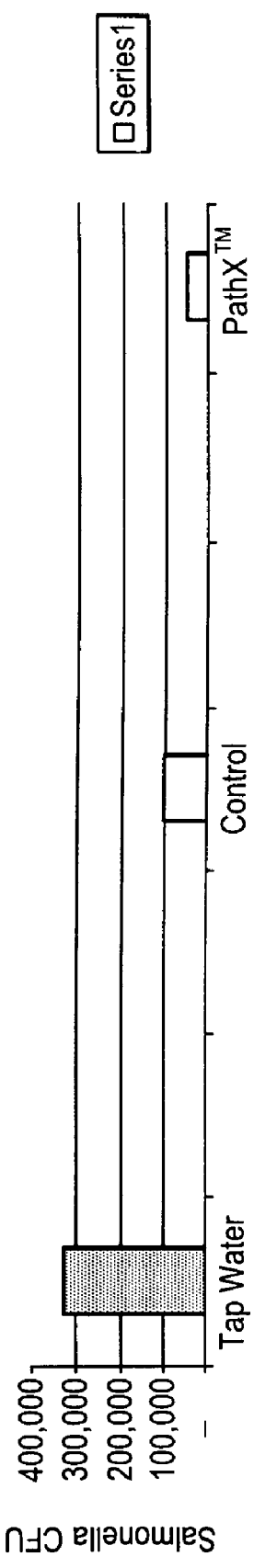
FIGS. 9 and 10 illustrate results of testing of the on-line reprocessing system for *E. coli* and *Salmonella* according to the present disclosure.
Figure 10:
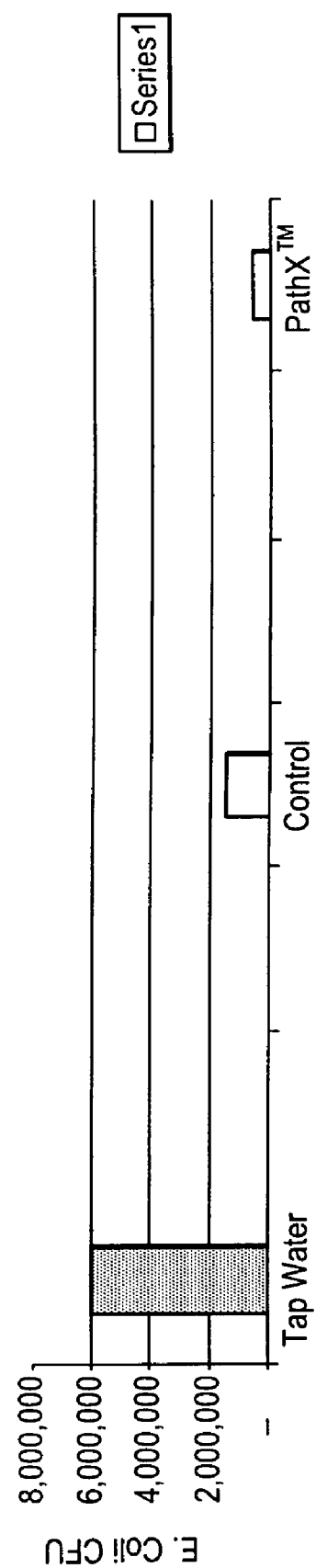

Table 14 and FIGS. 9 and 10 display the data collected in the above experimental procedures. When averaged, the data indicates that the on-line reprocessing system tank (i.e., the PathX™ system) shows substantial disinfection improvement over the tap water tank and the control tank. Individually, the second and third trials, where the chlorine concentration was maintained constant, show the greatest improvement.

TABLE 14

|  | Tap Water | Uncontrolled pH | PathX ™ |
|---|---|---|---|
| Salmonella (CFU) | 333,367 | 103,225 | 50,437 |
| E. coli (CFU) | 5,900,219 | 1,429,790 | 625,989 |

These two sets of experiments demonstrate that the on-line reprocessing system technique of a neutral controlled pH and a consistent chlorine concentration can provide improved disinfection when compared to the tap water and control tanks. Current chlorine chemistry theory supports these results. At a neutral pH, the majority of available chorine is in the form of hypochlorous acid. The hypochlorous acid reacts more quickly than hypochlorite to reduce microorganism populations.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method for recycling water used in the processing of poultry comprising the steps of:
    recovering a portion of water used in a non-chilling processing step of poultry processing, said step of recovering water includes passing said water through a recovery sump comprising a basin having a first compartment for receiving said recovered water and barrier in said basin forming a second compartment, said first compartment having a means for skimming solids from said recovered water leaving skimmed water that flows into said second compartment, said second compartment having means for allowing said skimmed water to exit said basin for further processing;
    treating said recovered water to reduce impurities and provide disinfection, said step of treating including reacting ozone with said recovered water to produce surfactants; and
    reusing said treated water in at least one other step of poultry processing.

2. The method according to claim 1, wherein said step of recovering water is from at least one step in said poultry processing selected from the group consisting of wash steps, non-final rinse steps, water sprays, flumes and final rinse step.

3. The method according to claim 1, wherein said step of treating water includes reacting ozone with said recovered water to produce surfactants and reduce the surface tension of said recovered water.

4. The method according to claim 1, wherein said step of treating includes removal of one or more contaminants selected from the group consisting of solid matter, floatable fats, oils, grease, lipids, blood proteins, carbohydrates, suspended and dissolved organic materials, animal parts and debris.

5. The method according to claim 1, wherein said treated water has a turbidity of less than or equal to 5 Nephelometric Turbidity Units (NTU).

6. The method of processing poultry according to claim 1, wherein said step of reusing said treated water includes introduction of said treated water into pores and membranes of poultry.

7. The method according to claim 1, wherein said recovery sump further comprises a filter for screening said recovered water prior to said recovered water being received by said first compartment, and said means for skimming solids communicates with a drain whereby the skimmed solids may be continuously removed from said recovered water.

8. The method according to claim 1, wherein said basin further comprises at least one drain outlet.

9. The method according to claim 1, wherein said basin comprises a plurality of compartments each, except said first compartment, in fluid communication with the preceding compartment, and each, except the last compartment having a means for skimming solids.

10. The method according to claim 1, wherein said step of treating further comprises the steps of:
    filtering said recovered water to remove non-dissolved components; and
    disinfecting said filtered water to limit its microbiological activity.

11. The method according to claim 1, further including a step of recovering a further portion of water used in a chilling processing step of poultry processing, whereby no more than approximately 40 percent of said recovered water originates in a chilling step.

12. A method for recycling water used in the processing of poultry comprising the steps of:
    recovering a portion of water used in a non-chilling processing step of poultry processing, said recovered water containing animal fats;
    treating said recovered water to reduce impurities and provide disinfection, said step of treating further including introducing ozone into said recovered water, wherein said introduction of said ozone saponifies said animal fats to produce a surfactant, introducing chlorine into said recovered water, and reacting said ozone and said chlorine with said recovered water to generate a biocide; and
    reusing said treated water in at least one other step of poultry processing.

13. A method for recycling water used in the processing of poultry comprising the steps of:
    recovering a portion of water used in a non-chilling processing step of poultry processing;
    treating said recovered water to reduce impurities and provide disinfection, said step of treating including introducing ozone and chlorine into said recovered water, said step of treating further including reacting said ozone and said chlorine with said recovered water to generate a biocide; and reusing said treated water in at least one other step of poultry processing.

14. The method of processing poultry according to claim 13, wherein said step of treating includes generating a chloramine via said reaction of said ozone and said chlorine with said recovered water.

15. The method of processing poultry according to claim 13, wherein said step of treating includes destroying bacteria and microorganisms from said recovered water.

16. The method of processing poultry according to claim 13, wherein said step of treating includes releasing and destroying bacteria and microorganisms from said poultry.

17. The method according to claim 13, wherein said treated water has a turbidity of less than or equal to 5 Nephelometric Turbidity Units (NTU).

18. The method according to claim 13, wherein said step of recovering water includes passing said water through a recovery sump comprising a basin having a first compartment for receiving said recovered water and barrier in said basin forming a second compartment, said first compartment having at least one weir pipe for skimming solids from the surface of said recovered water leaving skimmed water which, when said skimmed water reaches a level higher than said barrier, flows into said second compartment, and wherein said second compartment has an exit orifice in fluid communication therewith for allowing said skimmed water to exit said basin for further processing.

19. The method according to claim 18, wherein said recovery sump further comprises a filter for screening said recovered water prior to said recovered water being received by said first compartment, and said weir pipe communicates with a drain whereby the skimmed solids may be continuously removed from said recovered water.

20. A method of processing poultry comprising the steps of:
   recovering water used in at least one processing step associated with processing poultry;
   treating said recovered water to reduce microorganisms within said poultry, said step of treating including introducing ozone and chlorine into said recovered water, reacting ozone with said recovered water to produce surfactants such that the surface tension of said recovered water about said poultry is reduced, said step of treating further including reacting said ozone and said chlorine with said recovered water to generate a biocide such that bacteria and microorganisms are released from said poultry and destroyed; and
   reintroducing said treated water into any of said at least one processing step whereby said treated water is introduced into said poultry and said introduction reduces the level of microorganisms within said poultry.

* * * * *